US009757203B2

(12) United States Patent
Hourtash et al.

(10) Patent No.: US 9,757,203 B2
(45) Date of Patent: Sep. 12, 2017

(54) MANIPULATOR ARM-TO-PATIENT COLLISION AVOIDANCE USING A NULL-SPACE

(71) Applicant: Intuitive Surgical Operations, Inc., Sunnyvale, CA (US)

(72) Inventors: Arjang M. Hourtash, Santa Clara, CA (US); Pushkar Hingwe, Fremont, CA (US); Bruce Michael Schena, Menlo Park, CA (US); Roman L. Devengenzo, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 15/351,254

(22) Filed: Nov. 14, 2016

(65) Prior Publication Data

US 2017/0056117 A1 Mar. 2, 2017

Related U.S. Application Data

(62) Division of application No. 13/906,713, filed on May 31, 2013, now Pat. No. 9,492,235.
(Continued)

(51) Int. Cl.
*G06F 19/00* (2011.01)
*A61B 34/30* (2016.01)
(Continued)

(52) U.S. Cl.
CPC .............. *A61B 34/30* (2016.02); *A61B 34/37* (2016.02); *B25J 9/1607* (2013.01); *B25J 9/1676* (2013.01);
(Continued)

(58) Field of Classification Search
None
See application file for complete search history.

(56) References Cited

U.S. PATENT DOCUMENTS 3,920,972 A 11/1975 Corwin, Jr. et al.
4,028,533 A 6/1977 Matsubara
(Continued)

FOREIGN PATENT DOCUMENTS

CN 1461693 A 12/2003
EP 1234641 A1 8/2002
(Continued)

OTHER PUBLICATIONS

Albu-Schäffer A., et al., "Parameter Identification and Passivity Based Joint Control for a 7DOF Torque Controlled Light Weight Robot," Proceedings of the 2001 IEEE, International Conference on Robotics and Automation, 2001, vol. 3, pp. 2852-2858.
(Continued)

*Primary Examiner* — Bhavesh V Amin
(74) *Attorney, Agent, or Firm* — Schwegman Lundberg & Woessner, P.A.

(57) ABSTRACT

Devices, systems, and methods for avoiding collisions between a manipulator arm and an outer patient surface by moving the manipulator within a null-space. In response to a determination that distance between an avoidance geometry and obstacle surface, corresponding to a manipulator-to-patient distance is less than desired, the system calculates movement of one or more joints or links of the manipulator within a null-space of the Jacobian to increase this distance. The joints are driven according to the reconfiguration command and calculated movement so as to maintain a desired state of the end effector. In one aspect, the joints are also driven according to a calculated end effector displacing movement within a null-perpendicular-space of the Jacobian to effect a desired movement of the end effector or remote
(Continued)

center while concurrently avoiding arm-to-patient collisions by moving the joints within the null-space.

20 Claims, 16 Drawing Sheets

Related U.S. Application Data

(60) Provisional application No. 61/654,755, filed on Jun. 1, 2012.

(51) Int. Cl.
    *B25J 9/16*           (2006.01)
    *A61B 34/37*        (2016.01)

(52) U.S. Cl.
    CPC .............. *A61B 2034/305* (2016.02); *G05B 2219/39135* (2013.01); *G05B 2219/40202* (2013.01); *G05B 2219/40371* (2013.01); *G05B 2219/40471* (2013.01); *G05B 2219/40492* (2013.01); *G05B 2219/45117* (2013.01)

(56) References Cited

U.S. PATENT DOCUMENTS

| | | |
|---|---|---|
| 4,063,073 A | 12/1977 | Strayer |
| 4,578,757 A | 3/1986 | Stark |
| 4,999,553 A | 3/1991 | Seraji |
| 5,086,401 A | 2/1992 | Glassman et al. |
| 5,130,632 A | 7/1992 | Ezawa et al. |
| 5,159,249 A | 10/1992 | Megherbi |
| 5,430,543 A | 7/1995 | Howard |
| 5,513,100 A | 4/1996 | Parker et al. |
| 5,550,953 A | 8/1996 | Seraji |
| 5,587,937 A | 12/1996 | Massie et al. |
| 5,632,758 A | 5/1997 | Sklar |
| 5,710,870 A | 1/1998 | Ohm et al. |
| 5,737,500 A | 4/1998 | Seraji et al. |
| 5,823,980 A | 10/1998 | Kopfer |
| 5,855,583 A | 1/1999 | Wang et al. |
| 5,908,458 A | 6/1999 | Rowe et al. |
| 6,037,927 A | 3/2000 | Rosenberg |
| 6,098,260 A | 8/2000 | Sarh |
| 6,246,200 B1 | 6/2001 | Blumenkranz et al. |
| 6,312,435 B1 | 11/2001 | Wallace et al. |
| 6,317,651 B1 | 11/2001 | Gerstenberger et al. |
| 6,331,181 B1 | 12/2001 | Tierney et al. |
| 6,377,011 B1 | 4/2002 | Ben-Ur |
| 6,379,073 B1 | 4/2002 | Yoo et al. |
| 6,400,115 B1 | 6/2002 | Yamazoe |
| 6,424,885 B1 | 7/2002 | Niemeyer et al. |
| 6,459,926 B1 | 10/2002 | Nowlin et al. |
| 6,468,265 B1 | 10/2002 | Evans et al. |
| 6,493,608 B1 | 12/2002 | Niemeyer |
| 6,645,196 B1 | 11/2003 | Nixon et al. |
| 6,678,582 B2 | 1/2004 | Waled |
| 6,699,177 B1 | 3/2004 | Wang et al. |
| 6,763,286 B2 | 7/2004 | Metelski |
| 6,786,896 B1 | 9/2004 | Madhani et al. |
| 7,083,571 B2 | 8/2006 | Wang et al. |
| 7,280,633 B2 | 10/2007 | Cheng et al. |
| 7,379,533 B2 | 5/2008 | Koertge |
| 7,428,296 B2 | 9/2008 | Bernhardt et al. |
| 7,564,949 B2 | 7/2009 | Sattler et al. |
| 7,646,161 B2 | 1/2010 | Albu-Schaffer et al. |
| 7,763,015 B2 | 7/2010 | Cooper et al. |
| 8,004,229 B2 | 8/2011 | Nowlin et al. |
| 8,041,459 B2 | 10/2011 | Sutherland et al. |
| 8,123,740 B2 | 2/2012 | Madhani et al. |
| 8,162,926 B2 | 4/2012 | Schena |
| 9,492,235 B2 | 11/2016 | Hourtash et al. |
| 2001/0013764 A1 | 8/2001 | Blumenkranz et al. |
| 2001/0018591 A1 | 8/2001 | Brock et al. |
| 2002/0082612 A1 | 6/2002 | Moll et al. |
| 2002/0111713 A1 | 8/2002 | Wang et al. |
| 2002/0120363 A1 | 8/2002 | Salisbury et al. |
| 2003/0018412 A1 | 1/2003 | Kimura et al. |
| 2003/0060927 A1 | 3/2003 | Gerbi et al. |
| 2003/0065311 A1 | 4/2003 | Wang et al. |
| 2003/0109780 A1 | 6/2003 | Coste-Maniere et al. |
| 2003/0139753 A1 | 7/2003 | Wang et al. |
| 2003/0216715 A1 | 11/2003 | Moll et al. |
| 2004/0034283 A1 | 2/2004 | Quaid, III |
| 2004/0039485 A1 | 2/2004 | Niemeyer et al. |
| 2004/0042583 A1 | 3/2004 | Wackerle et al. |
| 2004/0111183 A1 | 6/2004 | Sutherland et al. |
| 2004/0186484 A1 | 9/2004 | Ryan |
| 2005/0104549 A1 | 5/2005 | Nishimura et al. |
| 2007/0162164 A1 | 7/2007 | Dariush |
| 2008/0037712 A1 | 2/2008 | Klingenbeck-Regn |
| 2009/0234444 A1 | 9/2009 | Maschke |
| 2009/0297011 A1 | 12/2009 | Brunner et al. |
| 2010/0191371 A1 | 7/2010 | Hornung et al. |
| 2011/0040306 A1 | 2/2011 | Prisco et al. |
| 2011/0218679 A1 | 9/2011 | Cheng et al. |
| 2011/0264108 A1 | 10/2011 | Nowlin et al. |
| 2011/0264109 A1 | 10/2011 | Nowlin et al. |
| 2011/0264110 A1 | 10/2011 | Nowlin et al. |
| 2011/0264111 A1 | 10/2011 | Nowlin et al. |
| 2011/0264112 A1 | 10/2011 | Nowlin et al. |
| 2011/0270271 A1 | 11/2011 | Nowlin et al. |
| 2011/0276059 A1 | 11/2011 | Nowlin et al. |
| 2013/0325029 A1* | 12/2013 | Hourtash ............... B25J 9/1607 606/130 |

FOREIGN PATENT DOCUMENTS

| | | |
|---|---|---|
| EP | 1951139 A2 | 8/2008 |
| EP | 1972415 A1 | 9/2008 |
| GB | 2311149 A | 9/1997 |
| JP | 2003159674 A | 6/2003 |
| WO | WO-9729690 A1 | 8/1997 |
| WO | WO-9950721 A1 | 10/1999 |
| WO | WO-02051329 A1 | 7/2002 |
| WO | WO-02060653 A9 | 12/2002 |
| WO | WO-2007076119 A2 | 7/2007 |
| WO | WO-2008015666 A2 | 2/2008 |
| WO | WO-2013078529 A1 | 6/2013 |

OTHER PUBLICATIONS

Albu-Schaffer, Alin and Gerd Hirzinger, "Cartesian Impedance Control Techniques for Torque Controlled Light-Weight Robots," IEEE International Conference on Robotics and Automation, IEEE, 2002, vol. 1, pp. 657-663.

Baerlocher, P. et al., "Task Priority Formulations for the Kinematic Control of Highly Redundant Articulated Structures," IEEE/RSJ International Conference on Intelligent Robots and Systems, 1998, pp. 323-329, vol. 1, IEEE.

Boyd, Stephen, "Convex Optimization," 2004, 8 pages, Cambridge University Press.

Da Vinci, Chirurgie-System Benutzerhandbuch, Intuitive Surgical Inc., 2004, 9 Chapters and 2 Appendixes, 260 pages.

English, James D. et al., "On the Implementation of Velocity Control for Kinematically Redundant Manipulators," IEEE transactions on systems, man, and cybernetics. Part A, Systems and humans, 2000, pp. 233-237, vol. 30-No. 3, IEEE.

Espiau, Bernard et al., "Collision Avoidance for Redundant Robots with Proximity Sensors," The Third International Symposium of Robotics Research, 1986, pp. 243-251, MIT Press.

European Search Report for Application No. EP10196665.3, mailed on Oct. 15, 2012, 8 pages.

European Search Report for Application No. EP10196666, mailed on Jul. 19, 2012, 7 pages.

European Search Report for Application No. EP10196670.3, mailed Oct. 26, 2012, 9 pages.

European Search Report for Application No. EP10196671, mailed on Oct. 15, 2012, 7 pages.

(56) References Cited

OTHER PUBLICATIONS

Extended EP Search Report and Written Opinion for Application No. EP10196669.5, mailed Jul. 26, 2012, 7 pages.
Extended European Search Report and Written Opinion for Application No. EP10196664.6, mailed on Jul. 25, 2012, 7 pages.
Extended European Search Report for Application No. EP101996666.1, mailed on Jul. 19, 2012, 7 pages.
Extended European Search Report for Application No. 13796945.7 mailed on Jan. 19, 2016, 11 pages.
Fratu A., et al., "Using the Redundant Inverse Kinematics System for Collision Avoidance", Electrical and Electronics Engineering (ISEEE), 2010 3rd International Symposium on, IEEE, Piscataway, NJ, USA, Sep. 16, 2010, pp. 88-93, XP031795460, ISBN: 978-1-4244-8406-5.
Grunwald G., et al., "Programming by Touch: The Different Way of Human-Robot Interaction," IEEE Transactions on Industrial Electronics, 2003, vol. 50 (4), pp. 659-666.
Hirzinger G., et al., "A Mechatronics Approach to the Design of Light-Weight Arms and Multifingered Hands," Proceedings of the 2000 IEEE, International Conference on Robotics and Automation, 2000, pp. 46-54.
Hirzinger G., et al., "On a New Generation of Torque Controlled Light-Weight Robots," Proceedings of the 2001 IEEE, International Conference on Robotics and Automation, 2001, pp. 3356-3363.
Howe R.D., et al., "Robotics for Surgery," Annual Review of Biomedical Engineering, 1999, vol. 1, pp. 211-240.
Interlink Electronics, "Force Sensing Resistors for Medical Equipment, Automotive, and Musical Instruments," 2003, 1 page, Internet: http://www.interlinkelec.com/products/fsr/fsr.htm (last visited Jul. 2003).
International Search Report and Written Opinion for Application No. PCT/US2006/017843, mailed on Jan. 4, 2007, 11 pages.
International Search Report and Written Opinion for Application No. PCT/US2013/043557, mailed on Sep. 6, 2013, 15 pages.
International Search Report and Written Opinion for Application No. PCT/US2013/043564, mailed on Sep. 6, 2013, 16 pages.
International Search Report and Written Opinion for Application No. PCT/US2013/043578, mailed on Sep. 5, 2013, 14 pages.
Kazanzides, Peter et al., "Force Sensing and Control for a Surgical Robot," Int. Conference on Robotics and Automation, May 1992, Nice, France; pp. 612-617, vol. 1, IEEE.
Khatib O., "A Unified Approach for Motion and Force Control of Robot Manipulators: The Operational Space Formulation," IEEE Journal of Robotics and Automation, 1987, vol. Ra-3 (1), pp. 43-53.
Konietschke R., et al., "A Preoperative Planning Procedure for Robotically Assisted Minimally Invasive Interventions," Lecture Notes in Computer Science, CURAC, 2004.
Konietschke R., et al., "Manipulability and Accuracy Measures for a Medical Robot in Minimally Invasive Surgery," Conference Proceeding, In proceeding of: 9th International Symposium on Advances in Robot Kinematics(ARK), Sestri Levante, Italy, Jun. 28-Jul. 1, 2004, 8 pages.
Krupa A., et al., "Towards Semi-Autonomy in Laparoscopic Surgery Through Vision and Force Feedback Control," Experimental Robotics VII, Lecture Notes in Control and Information Sciences, 2001, vol. 271, pp. 189-198.

Maciejewski A.A., et al., "Obstacle Avoidance for Kinematically Redundant Manipulators in Dynamically Varying Environments," International Journal of Robotics Research, 1985, vol. 4 (3), pp. 109-117.
Maciejewski, Anthony A. et al., "The Singular Value Decomposition: Computation and Applications to Robotics," The International Journal of Robotics Research, 1989, pp. 63-79, vol. 8-No. 6, Sage Publications.
Michelin M., et al., "Dynamic Task/Posture Decoupling for Minimally Invasive Surgery Motions," Intelligent Robots and Systems, 2004, vol. 4, pp. 3625-3630.
Monnich, Holger et al., "OP:Sense; Research platform for semi-autonomous robot-assisted surgery with haptic feedback and optical supervision" [online video], 2011 [retrieved on Jun. 12, 2013]. Retrieved from the Internet:< URL: https://www.youtube.com/watch?v=g0ZgSaNtTUw.
Nakamura Y., et al., "Task-Priority Based Redundancy Control of Robot Manipulators," International Journal of Robotics Research, Sage Science Press, Thousand Oaks, US, Jun. 21, 1987, vol. 6 (2), pp. 3-15.
Office Action mailed Jul. 20, 2016 for Chinese Application No. 201380027983.1 filed May 31, 2013, 19 pages.
Ortmaier T.J., "Motion Compensation in Minimally Invasive Robotic Surgery," 2002, 5 Chapters, 147 pages.
Schreiber G., "Interactive Redundant Robotics: Control of the Inverted Pendulum with Nullspace Motion," Proceedings of the 2001, IEEE/RSJ, International Conference on Intelligent Robots and Systems, 2001, pp. 158-164.
Schreiber G., Steuerung fur Redundante Robotersysteme: Benutzer und Aufgabenorientierte Verwendung Der Redundanz, 2004, 296 pages.
Siciliano B., "Kinematic Control of Redundant Robot Manipulators: A Tutorial" Journal of Intelligent and Robotic Systems, 1990, vol. 3 (3), pp. 201-212.
Siciliano, Bruno et al., "A General Framework for Managing Multiple Tasks in Highly Redundant Robotic Systems," Fifth International Conference of Advanced Robotics, 1991, pp. 1211-1216, IEEE.
Smalley, Eric, "Flexible sensors make robot skin," Technology Research News, Sep. 22/29, 2004, 3 pages, Internet: http://www.trnmag.com/Stories/2004/092204/Flexible_sensors_make_robot_skin%20_092204.html (last visited Dec. 17, 2004).
Stanford University, Dexterous Manipulation Laboratory, "The 'Capaciflector' Proximity Sensor" 2005, 3 pages, Internet: http://www.cdr.stanford.edu/Touch/previous_projects/capaciflector/capaciflector.htm (last visited Jan. 5, 2005).
Tapeswitch Corporation, Data Sheet for Controflex Ribbon Switches, last downloaded Dec. 17, 2004, 2 pages, Internet: http://www.tapeswitch.com/products/contflex.php.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Yigit S., et al., "Specific Combined Control Mechanisms for Human Robot Co-Operation," Institute for Process Control and Robotics (IPR), 2003, 6 pages.

* cited by examiner

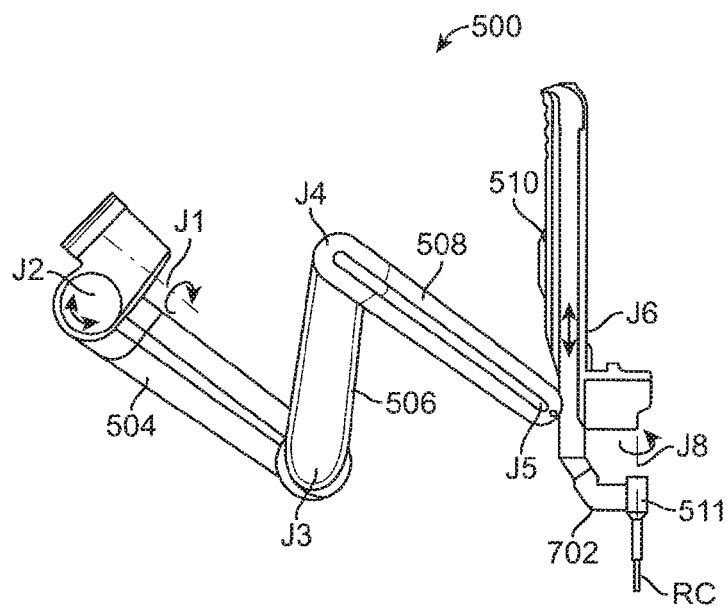
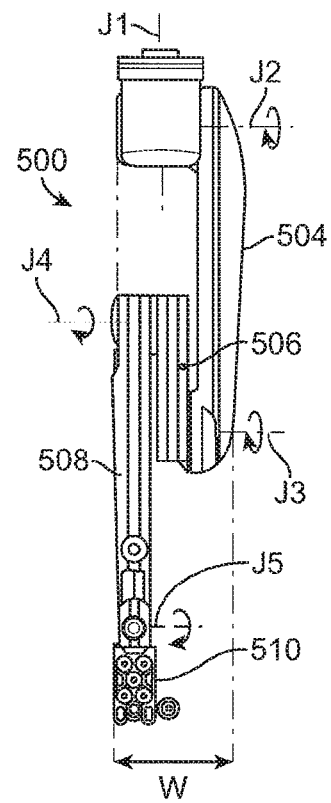
FIG. 5B
FIG. 5D
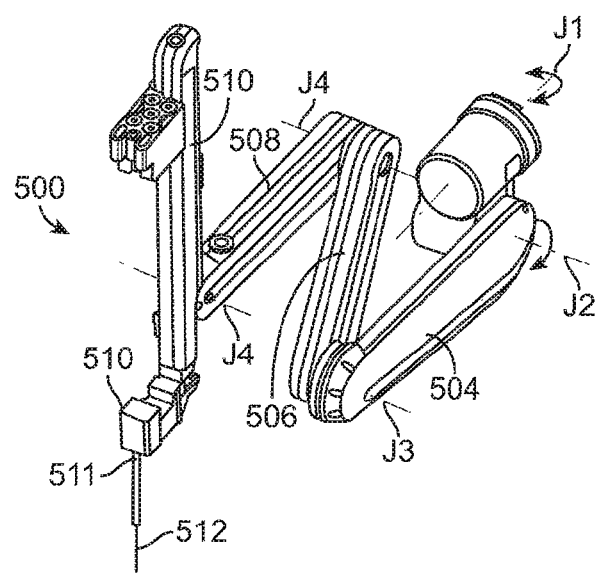
FIG. 5C

MANIPULATOR ARM-TO-PATIENT COLLISION AVOIDANCE USING A NULL-SPACE

CROSS-REFERENCES TO RELATED APPLICATIONS

This application is a divisional of U.S. application Ser. No. 13/906,713, filed May 31, 2013, which is a Non-Provisional of and claims the benefit of priority from U.S. Provisional Patent Application No. 61/654,755, filed on Jun. 1, 2012, and entitled "Manipulator Arm-to-Patient Collision Avoidance Using a Null-Space," the full disclosure of each of which is incorporated herein by reference in its entirety.

The present application is generally related to the following commonly-owned applications: U.S. application Ser. No. 12/494,695 filed Jun. 30, 2009, entitled "Control of Medical Robotic System Manipulator About Kinematic Singularities;" U.S. application Ser. No. 12/406,004 filed Mar. 17, 2009, entitled "Master Controller Having Redundant Degrees of Freedom and Added Forces to Create Internal Motion;" U.S. application Ser. No. 11/133,423 filed May 19, 2005 (U.S. Pat. No. 8,004,229), entitled "Software Center and Highly Configurable Robotic Systems for Surgery and Other Uses;" U.S. application Ser. No. 10/957,077 filed Sep. 30, 2004 (U.S. Pat. No. 7,594,912), entitled "Offset Remote Center Manipulator For Robotic Surgery;" U.S. application Ser. No. 09/398,507 filed Sep. 17, 1999 (U.S. Pat. No. 6,714,839), entitled "Master Having Redundant Degrees of Freedom;" and U.S. application Ser. No. 13/906,767 entitled "System and Methods for Commanded Reconfiguration of a Surgical Manipulator Using the Null-Space;" and Ser. No. 13/906,819 entitled "Systems and Methods for Avoiding Collisions Between Manipulator Arms Using a Null-Space" filed May 31, 2013; the disclosures of which are incorporated herein by reference in their entireties.

BACKGROUND OF THE INVENTION

The present invention generally provides improved surgical and/or robotic devices, systems, and methods.

Minimally invasive medical techniques are aimed at reducing the amount of tissue which is damaged during diagnostic or surgical procedures, thereby reducing patient recovery time, discomfort, and deleterious side effects. Millions of "open" or traditional surgeries are performed each year in the United States; many of these surgeries can potentially be performed in a minimally invasive manner. However, only a relatively small number of surgeries concurrently use minimally invasive techniques due to limitations in minimally invasive surgical instruments and techniques and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, often the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulator arms are included for moving an endoscope or other image capture device, additional surgical instruments, or the like.

A variety of structural arrangements can be used to support the surgical instrument at the surgical site during robotic surgery. The driven linkage or "slave" is often called a robotic surgical manipulator, and example linkage arrangements for use as a robotic surgical manipulator during minimally invasive robotic surgery are described in U.S. Pat. Nos. 6,758,843; 6,246,200; and 5,800,423, the full disclosures of which are incorporated herein by reference. These linkages often make use of a parallelogram arrangement to hold an instrument having a shaft. Such a manipulator structure can constrain movement of the instrument so that the instrument shaft pivots about a remote center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 6,702,805; 6,676,669; 5,855,583; 5,808,665; 5,445,166; and 5,184,601, the full disclosures of which are incorporated herein by reference.

While the new robotic surgical systems and devices have proven highly effective and advantageous, still further improvements would be desirable. For example, when moving the surgical instruments within a minimally invasive surgical site, robotic surgical manipulators may exhibit a significant amount of movement outside the patient, particularly when pivoting instruments about minimally invasive apertures through large angular ranges, which can lead to the moving manipulators inadvertently coming into contact with each other, with instrument carts or other structures in the surgical room, with surgical personnel, and/or with the outer surface of the patient. In particular, the manipulator arm near a distal instrument may inadvertently contact the outer patient surface as the manipulator pivots about the minimally invasive aperture. Alternative highly configurable "software center" surgical manipulator systems have been proposed and may provide significant advantages, but may also present different challenges. In particular, the proposed software center systems may not have all the safety advantages of the mechanically constrained remote-center linkages in some conditions. Regardless, as the range of surgeries being performed using telesurgical systems continues to expand, there is an increasing demand for expanding the available configurations and the range of motion of the instruments within the patient. Unfortunately, both of these changes can increase the challenges associated with controlling and predicting the motion of the manipulators outside the body, and increase the importance of avoiding undesirable contact or collision between components of the manipulator arm and an outer surface of the patient.

For these and other reasons, it would be advantageous to provide improved devices, systems, and methods for surgery, robotic surgery, and other robotic applications. It would be particularly beneficial if these improved technologies provided the ability to avoid collisions between the manipulator arm and the patient while maintaining a desired end effector state or a desired location of a remote center about which the instrument shaft pivots. Ideally, these improvements would allow for improved movement of one or more manipulator arms during a surgical procedure while avoiding collisions between the manipulator arms and the patient during end effector movement. Additionally, it would be desirable to provide such improvements while increasing the range of motion of the instruments for at least some procedures and without significantly increasing the size, mechanical complexity, or costs of these systems, and while maintaining or improving their dexterity.

BRIEF SUMMARY OF THE INVENTION

The present invention generally provides improved robotic and/or surgical devices, systems, and methods. In one aspect, the invention will employ highly configurable surgical robotic manipulators. These manipulators, for example, may have more degrees of freedom of movement than the associated surgical end effectors have within a surgical workspace of a patient. A robotic surgical system in accordance with the present invention typically includes a manipulator arm supporting a robotic surgical instrument and a processor to calculate coordinated joint movements for manipulating an end effector of the instrument. The joints of the robotic manipulators supporting the end effectors allow the manipulator to move throughout a range of different configurations for a given end effector position and/or a given pivot point location. The system allows for movement of the highly configurable robotic manipulators to avoid collisions with the patient by driving one or more joints of the manipulator according to coordinated movement of the joints calculated by a processor, which extends one or more joints of the manipulator within a null-space of the kinematic Jacobian so as to maintain the desired end effector state and/or pivot point location. Typically, the avoidance movement is calculated in response to a determination that a distance between the manipulator arm and an outer patient surface is less than desired.

In one aspect, a redundant degrees of freedom (RDOF) surgical robotic system with manipulate input is provided. The RDOF surgical robotic system comprises a manipulator assembly, one or more user input devices, and a processor with a controller. A manipulator arm of the assembly has a plurality of joints providing sufficient degrees of freedom that allow a range of joint states for a given end effector state. In response to a determination that a portion of the manipulator arm proximal of the distal end effector or remote center is too close to an outer surface of the patient, the system calculates an avoidance movement of the plurality of joints within the null-space. The processor is configured to then drive the joints, using a controller, according to the calculated avoidance movement so as to maintain a desired state of the end effector and/or remote center location. Often concurrently with the avoidance movement, in response to receiving a manipulation command to move the end effector with a desired movement, the system calculates end effector displacing movement of the joints by calculating joint movement within a null-perpendicular-space orthogonal to the null-space of the Jacobian, and drives the joints according to the calculated displacement movement to effect the desired end effector movement.

In another aspect of the present invention, the manipulator is configured to move such that an intermediate portion of the instrument shaft pivots about a remote center. Between the manipulator and the instrument, there are a plurality of driven joints providing sufficient degrees of freedom to allow a range of joint states for an end effector position as the intermediate portion of the instrument shaft extends through an access site. A processor having a controller couples the input device to the manipulator. In response a determination that a portion of the manipulator arm is too close to an outer surface of the patient, the processor determines movements of one or more joints to increase the distance between the portion of the manipulator arm and the outer surface of the patient so that the intermediate portion of the instrument is within the access site and to maintain the desired remote center location about which the shaft pivots. Typically, in response to receiving a manipulation command to effect a desired end effector's movement, the system calculates end effector displacing movement of the joints, which comprises calculating joint velocities within a null-perpendicular-space of the Jacobian orthogonal to the null-space, and then drives the joints according to the calculated movement to effect the desired end effector movement in which the instrument shaft pivots about the remote center, often concurrently with driving of the joints according to the calculated avoidance movement.

In one embodiment, the system defines an avoidance geometry corresponding to a state of one or more features of the manipulator arm and an obstacle surface corresponding to the location of the outer surface of a patient, and determines the nearest distance between the manipulator arm and outer patient surface by determining a distance between the avoidance geometry and the obstacle surface. In certain embodiments, the avoidance geometry includes one or more reference points, segments or volumes (e.g. solid bodies, a string of spheres, cylinders, etc.), or any suitable geometry corresponding to portions of the manipulator arm. For example, the avoidance geometry may include a reference point indicative of a state of a feature (e.g. a protruding portion) near the distal end of the manipulator, the state being a position or velocity of the feature, that may be determined using joint state sensors of the arm. The obstacle surface may comprise a plane extending through a distal portion of the arm, preferably the remote center location about which an instrument of the arm pivots, or a modeled surface, such as a cylindrical, spherical or convex surface that extends through one or more remote center locations corresponding to one or more manipulator arm instrument shafts.

In certain embodiments, in response to a determination that a distance between the avoidance geometry and the obstacle surface is less than a desired distance, which may be a pre-determined distance or a function of joint states, a processor of the system calculates an avoidance movement of the joints or links of the manipulator arm to increase the distance between the avoidance geometry and the obstacle surface and moving the joints or links within a null-space of the Jacobian so as to maintain the state of the end effector and/or location of a remote center of the manipulator arm. The desired state of the end effector may include a desired position, velocity or acceleration of the end effector. In some embodiments, the end effector manipulation command is received from an input device by a user, such as a surgeon entering the command on a surgical console master input, while the avoidance movement is calculated and used to drive the joints to provide sufficient clearance between the outer patient surface and the designated portions of the manipulator arm when the distance between the proximal portions of the manipulator arm and the outer patient surface is less than desired.

In an example embodiment, the manipulator arm includes a joint that pivots or twists an insertion axis of the instrument tool about its axis, the axis extending through a remote center about which a shaft of the instrument pivots. Ideally, the avoidance movement is calculated so as to drive this joint so as twist or pivot the feature, away from the outer patient surface while maintaining the state of the end-effector. In some embodiments, the displacement movement of the manipulator arm, calculated in response to a manipulation command, is calculated to avoid driving the joint or to avoid driving the twisting joint to effect the displacement movement. This aspect of calculating the avoidance movement to drive a particular joint that is not driven in the calculated displacement movement or vice versa may be applied to any of the joints of the manipulator arm described herein.

In certain embodiments, a revolute joint couples the proximal portion of the manipulator to the base and supports the manipulator arm such that joint movement of the revolute joint pivots one or more joints of the manipulator arm about a pivotal axis of the revolute joints. In some embodiments, the pivotal axis of the revolute joint extends from the joints toward the remote center, optionally through a remote center about which an instrument shaft of the end effector pivots. In one aspect, movement of the revolute joint pivots one or more joints of the manipulator arm about a cone distally tapered and oriented towards the remote center. The cone around which the manipulator arm pivots in this aspect, corresponds to the cone shaped void within the range of motion of the tool tip, in which the movement of the tool may be impossible or impaired. In another aspect, the joint coupling the proximal portion of the manipulator to the base is moveable relative to the base along a path, typically an arcuate or substantially circular path such that movement of the joint along the path pivots one or more joints of the manipulator arm about an axis extending toward a remote center about which the instrument shaft pivots. In some embodiments, the manipulator includes a revolute joint coupling the proximal portion of the manipulator to the base, the revolute joint being moveable relative to the base along a path, which may be linear, arcuate or substantially circular.

In yet another aspect of the present invention, a surgical robotic manipulator with a proximal revolute joint and a distal parallelogram linkage is provided, the pivotal axis of the revolute joint substantially intersecting with the axis of the instrument shaft of the end effector, optionally at a remote center if applicable. The system further includes a processor having a controller coupling the input to the manipulator arm and configured to calculate the avoidance movement of the plurality of joints as in any of the embodiments described herein.

A further understanding of the nature and advantages of the present invention will become apparent by reference to the remaining portions of the specification and drawings.

BRIEF DESCRIPTION OF THE DRAWINGS

FIGS. 5A-5D show an example manipulator arm.

DETAILED DESCRIPTION OF THE INVENTION

Figure 1A:
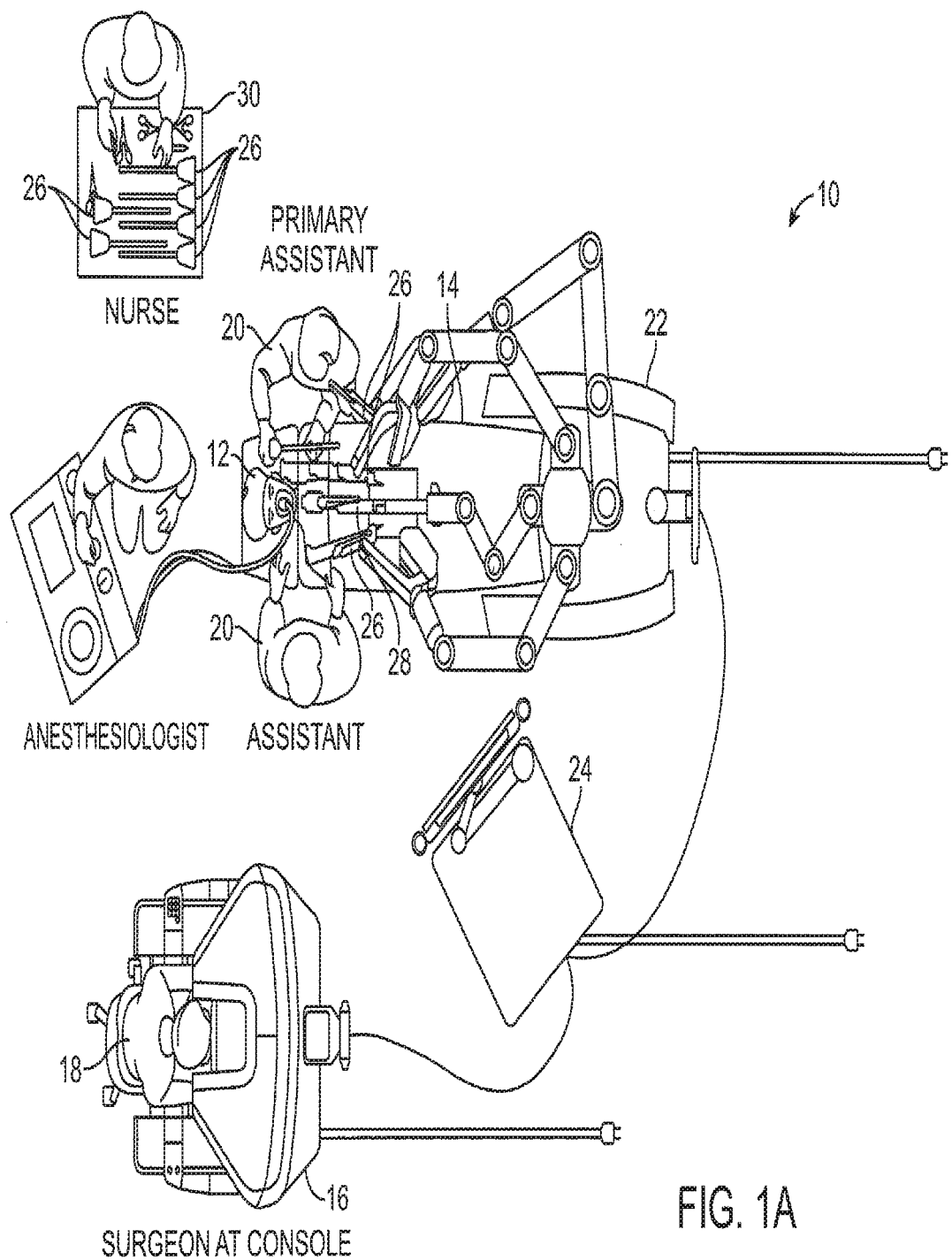
FIG. 1A is an overhead view of a robotic surgical system in accordance with embodiments of the present invention, the robotic surgical system having a surgical station with a plurality of robotic manipulators for robotically moving surgical instruments having surgical end effectors at an internal surgical site within a patient.

The present invention generally provides improved surgical and robotic devices, systems, and methods. The invention is particularly advantageous for use with surgical robotic systems in which a plurality of surgical tools or instruments will be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. The large number of degrees of freedom allow for reconfiguration of the linkages of the manipulator assemblies within a null-space of a kinematic Jacobian so as to move the linkages away from an outer patient surface while maintaining the desired end effector state. In some embodiments, the system determines when a distance between a portion of the manipulator arm and an outer patient surface is less than desired, and then drives the joints according to a calculated avoidance movement that extends the joints within a respective null-space so as to move the manipulator arm away from the outer patient surface. Often, the joints of the manipulator arm are driven according to the calculated avoidance movement concurrently with commanded displacement movement of a distal end effector during a surgical procedure.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site into a surgical workspace, rotation of the shaft about its axis, and pivotal motion of the shaft about a pivot point adjacent the access site.

Many of the example manipulator assemblies described herein have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation-plus three degrees of freedom to comply with the access site constraints), but may have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly within the null-space.

The invention provides robotic linkage structures which are particularly well suited for surgical (and other) applications in which a wide range of motion is desired, and for which a limited dedicated volume is available due to the presence of other robotic linkages, surgical personnel and equipment, and the like. The large range of motion and reduced volume needed for each robotic linkage may also provide greater flexibility between the location of the robotic support structure and the surgical or other workspace, thereby facilitating and speeding up setup.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Many aspects of control system that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, and/or the like.

In certain embodiments, the tool of an example manipulator arm pivots about a pivot point adjacent a minimally invasive aperture. In some embodiments, the system may utilize a hardware remote center, such as the remote center kinematics described in U.S. Pat. No. 6,786,896, the contents of which are incorporated herein in its entirety. Such systems may utilize a double parallelogram linkage which constrains movement of the linkages such that the shaft of the instrument supported by the manipulator pivots about a remote center point. Alternative mechanically constrained remote center linkage systems are known and/or may be developed in the future. Surprisingly, work in connection with the present invention indicates that remote center linkage systems may benefit from highly configurable kinematic architectures. In particular when a surgical robotic system has a linkage that allows pivotal motion about two axes intersecting at or near a minimally invasive surgical access site, the spherical pivotal motion may encompass the full extent of a desired range of motion within the patient, but may still suffer from avoidable deficiencies (such as being poorly conditioned, being susceptible to arm-to-arm or arm-to-patient contact outside the patient, and/or the like). At first, adding one or more additional degrees of freedom that are also mechanically constrained to pivotal motion at or near the access site may appear to offer few or any improvements in the range of motion. Nonetheless, such joints can provide significant advantages by allowing the overall system to be configured in or driven toward a collision-inhibiting pose, by further extending the range of motion for other surgical procedures, and the like. In other embodiments, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a calculated pivot point location, as opposed to pivot point determined by a mechanical constraint. By having the capability to compute software pivot points, different modes characterized by the compliance or stiffness of the system can be selectively implemented. More particularly, different system modes over a range of pivot points/centers (e.g., moveable pivot points, passive pivot points, fixed/rigid pivot point, soft pivot points) can be implemented as desired; thus, embodiments of the present invention are suitable for use in various types of manipulator arms, including software center arms and hardware center arms.

Despite the many advantages of a robotic surgical system having multiple highly configurable manipulators, since the manipulators include a relatively large number of joints and links between the base and instrument, movement of the manipulator arms can be particularly complex. As the range of configurations and range of motion of the manipulator arm increases no does the likelihood of arm-to-patient collisions between a portion of the manipulator arm proximal of the distal end effector and an outer surface of the patient. For example, the considerable range of motion of a manipulator arm having a distal tool that pivots about a remote center adjacent a minimally invasive aperture, as described herein, can allow a feature of the manipulator arm or a distal link of the manipulator arm itself to contact and/or collide with an outer surface of the patient. Since it can be difficult for a user to predict when such contact might occur due to the complexity of the movement of the manipulator arm, the present invention avoids such arm-to-patient collisions by calculating an avoidance movement of the manipulator arm and driving the joints to effect the avoidance movement while maintaining the desired state of a distal portion or tool of the manipulator arm.

Embodiments of the invention include a processor that calculates an avoidance movement which facilitates use of driven joints of the kinematic linkage to reconfigure the manipulator structure within a null-space of the Jacobian so as to avoid arm-to-patient collisions, typically in response to a determination that a distance between a reference or avoidance geometry of the manipulator arm and the patient surface is insufficient. In one aspect, the system determines the distance between the manipulator arm and an outer patient surface by analyzing the relationship between a defined "avoidance geometry" and an "obstacle surface," the avoidance geometry corresponding to one or more references on the manipulator arm and the obstacle surface corresponding to the outer patient surface. In some embodiments, the system determines a distance between the avoidance geometry and the obstacle surface, and if the distance is less than a desired distance (x) the system calculates an avoidance movement of the kinematic chain so as to maintain at least the desired distance between the reference geometry and the obstacle surface. The desired distance (x) may be a pre-determined distance, or may be a range of distances based on a given joint state or states. For example, the desired distance may change depending on the velocity of the joint near the patient surface or for a particular configuration of the manipulator arm near the patient.

In certain embodiments, the reference geometry includes one or more reference points that correspond to one or more protrusions or features relating to the manipulator arm, and the obstacle surface is an approximation or modeled surface corresponding to the outer patient surface during the surgical procedure. Typically, the reference geometry includes one or more points corresponding to a feature of a distal portion of the manipulator arm near the distal tool, such as a distal joint. Although typically the avoidance movement is a calculated movement that is separate from the calculated manipulation movement, the movements are combined by a controller so as to effect the avoidance movement concurrently with a commanded end effector manipulation movement. A controller of the surgical system may include a processor with a readable memory having joint controller programming instructions or code recorded thereon that allows the processor to derive suitable joint commands for driving the joints so as to allow the controller to effect the desired reconfiguration to avoid collision with the outer surface of the patient and/or to effect the desired end effector movement In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1B:
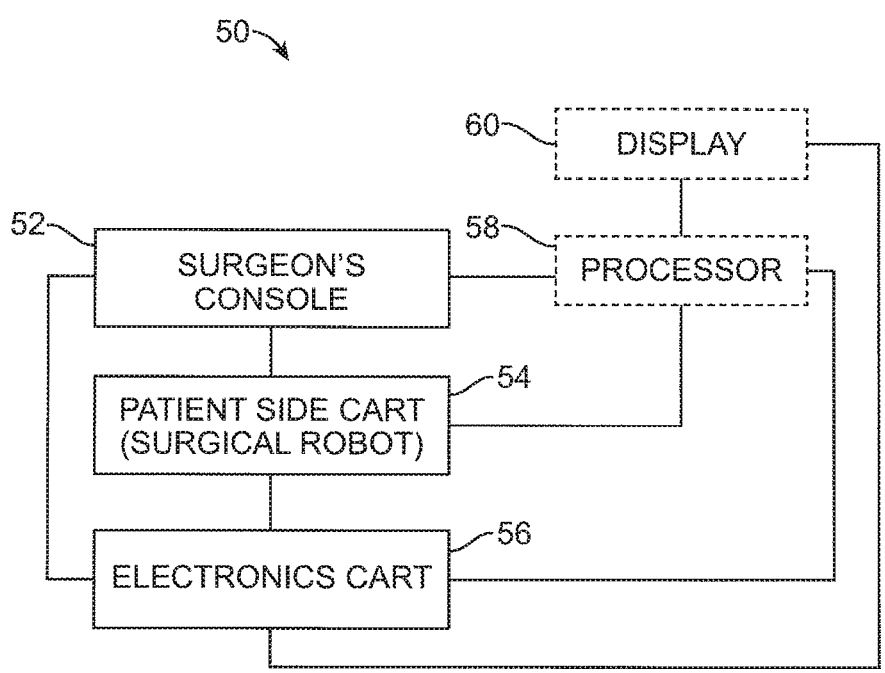
FIG. 1B diagrammatically illustrates the robotic surgical system of FIG. 1A.

Referring now to the drawings, in which like reference numerals represent like parts throughout the several views, FIG. 1A is an overhead view illustration of a Minimally Invasive Robotic Surgical (MIRS) system 10, in accordance with many embodiments, for use in performing a minimally invasive diagnostic or surgical procedure on a Patient 12 who is lying down on an Operating table 14. The system can include a Surgeon's Console 16 for use by a surgeon 18 during the procedure. One or more Assistants 20 may also participate in the procedure. The MIRS system 10 can further include a Patient Side Cart 22 (surgical robot and an Electronics Cart 24. The Patient Side Cart 22 can manipulate at least one removably coupled tool assembly 26 (hereinafter simply referred to as a "tool") through a minimally invasive incision in the body of the Patient 12 while the surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can he used to process the images of the surgical site for subsequent display to the surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room, FIG. 1B diagrammatically illustrates a robotic surgery system 50 (such as MIRS system 10 of FIG. 1A). As discussed above, a Surgeon's Console 52 (such as Surgeon's Console 16 in FIG. 1A) can be used by a surgeon to control a Patient Side Cart (Surgical Robot) 54 (such as Patent Side Cart 22 in FIG. 1A) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1A). As discussed above, the Electronics Cart 56 can process the captured images in a variety of ways prior to any subsequent display. For example, the Electronics Cart 56 can overlay the captured images with a virtual control interface prior to displaying the combined images to the surgeon via the Surgeon's Console 52. The Patient Side Cart 54 can output the captured images for processing outside the Electronics Cart 56. For example, the Patient Side Cart 54 can output the captured images to a processor 58, which can he used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 2:
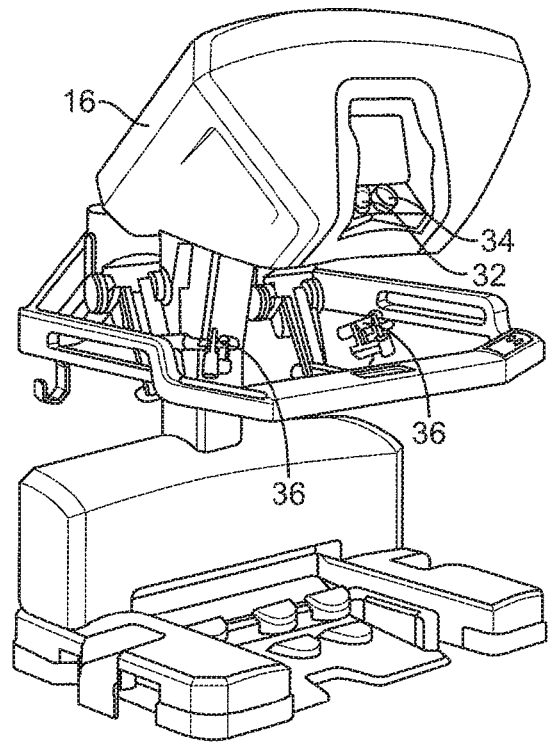
FIG. 2 is a perspective view illustrating a master surgeon console or workstation for inputting surgical procedure commands in the surgical system of FIG. 1A, the console including a processor for generating manipulator command signals in response to the input commands.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 own in FIG. 1A) to manipulate one or more tools. The input control devices 36 can provide the same degrees of freedom as their associated tools 26 (shown in FIG. 1A) so as to provide the surgeon with telepresence, or the perception that the input control devices 36 are integral with the tools 26 so that the surgeon has a strong sense of directly controlling the tools 26. To this end, position, force, and tactile feedback sensors (not shown) may be employed to transmit position, force, and tactile sensations from the tools 26 back to the surgeon's hands through the input control devices 36.

The Surgeon's Console 16 is usually located in the same room as the patient so that the surgeon may directly monitor the procedure, be physically present if necessary, and speak to an Assistant directly rather than over the telephone or other communication medium. However, the surgeon can be located in a different room, a completely different building, or other remote location from the Patient allowing for remote surgical procedures.

Figure 3:
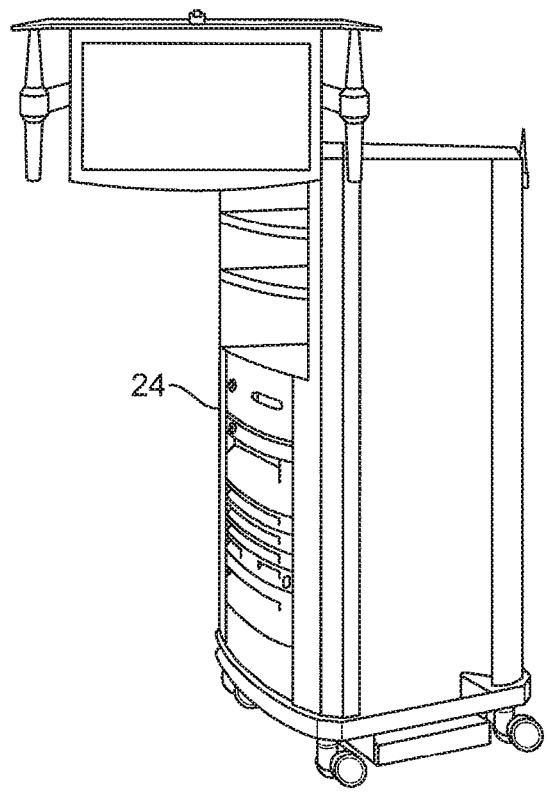
FIG. 3 is a perspective view of the electronics cart of FIG. 1A.
Figure 4:
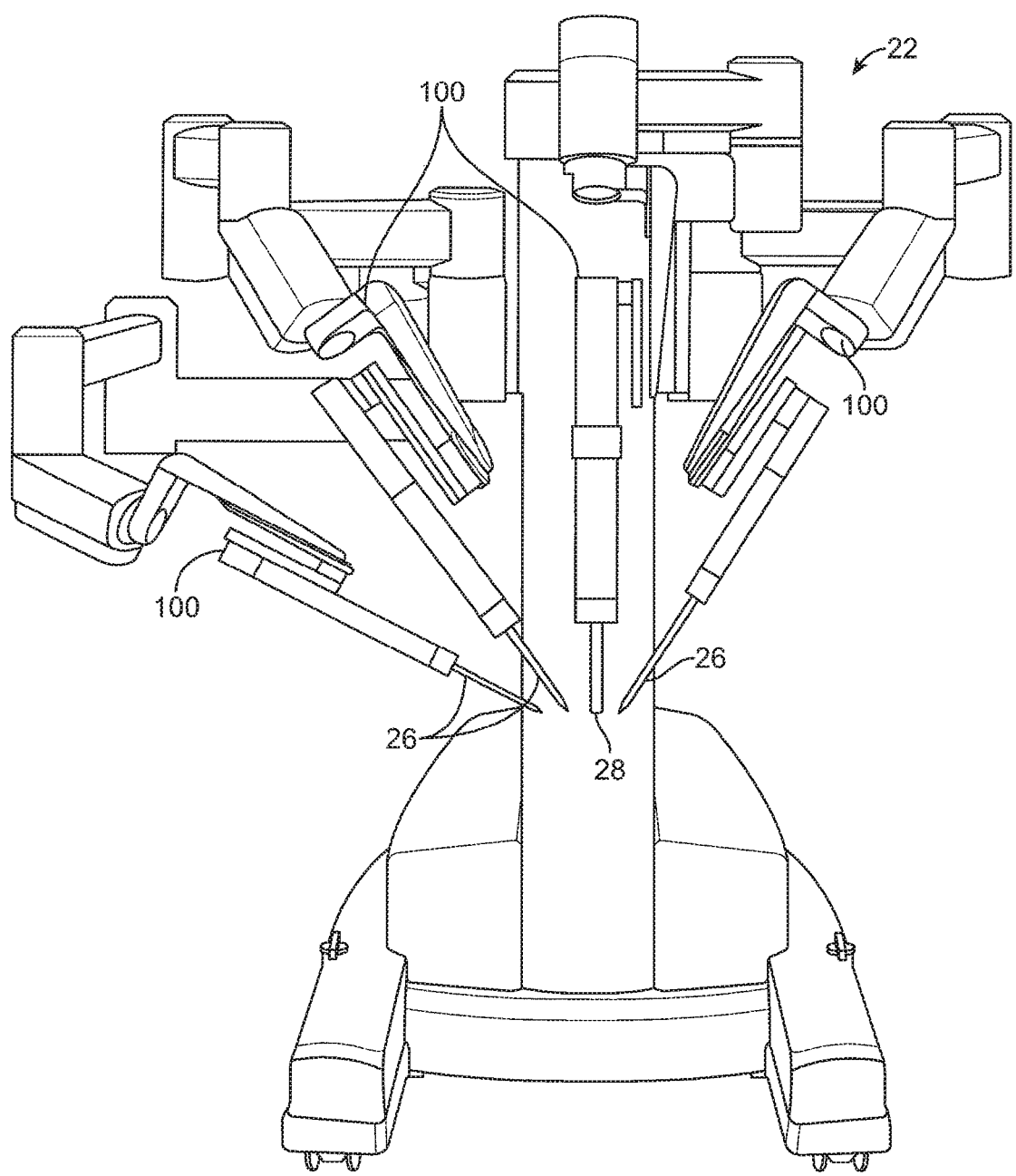
FIG. 4 is a perspective view of a patient side cart having four manipulator arms.

FIG. 3 is a perspective view of the Electronics Cart 24. The Electronics Cart 24 can be coupled with the endoscope 28 and can include a processor to process captured images for subsequent display, such as to a surgeon on the Surgeon's Console, or on another suitable display located locally and/or remotely. For example, where a stereoscopic endoscope is used, the Electronics Cart 24 can process the captured images so as to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations, FIG. 4 shows a Patient Side Cart 22 having a plurality of manipulator arms, each supporting a surgical instrument or tool 26 at a distal end of the manipulator arm. The Patient Side Cart 22 shown includes four manipulator arms 100 which can be used to support either a surgical tool 26 or an imaging device 28, such as a stereoscopic endoscope used for the capture of images of the site of the procedure. Manipulation is provided by the robotic manipulator arms 100 having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical instruments or tools 26 when they are positioned within the field-of-view of the imaging device 28.

Regarding surgical tool 26, a variety of alternative robotic surgical tools or instruments of different types and differing end effectors may be used, with the instruments of at least some of the manipulators being removed and replaced during a surgical procedure. Several of these end effectors, including DeBakey Forceps, microforceps, Potts scissors, and clip-applier include first and second end effector elements which pivot relative to each other so as to define a pair of end effector jaws (or blades). For instruments having end effector jaws, the jaws will often be actuated by squeezing the grip members of handle. Other end effectors, including scalpel and electrocautery probe have a single end effector element (e.g. a single "finger"). Single end effector instruments may also be actuated by gripping of the grip members, for example, so as to trigger the delivery of electrocautery energy to the instrument tip.

The elongate shaft of instrument 26 allow the end effectors and the distal end of the shaft to be inserted distally into a surgical worksite through a minimally invasive aperture, often through an abdominal wall or the like. The surgical worksite may be insufflated, and movement of the end effectors within the patient will often be effected, at least in part, by pivoting of the instrument 26 about the location at which the shaft passes through the minimally invasive aperture. In other words, manipulators 100 will move the proximal housing of the instrument outside the patient so that shaft extends through a minimally invasive aperture location so as to help provide a desired movement of end effector. Hence, manipulators 100 will often undergo significant movement outside patient P during a surgical procedure.

Example manipulator arms in accordance with many embodiments of the present invention can be understood with reference to FIGS. 5A-13C. As described above, a manipulator arm generally supports a distal instrument or surgical tool and effects movements of the instrument relative to a base. As a number of different instruments having differing end effectors may be sequentially mounted on each manipulator during a surgical procedure (typically with the help of a surgical assistant), a distal instrument holder will preferably allow rapid removal and replacement of the mounted instrument or tool. As can be understood with reference to FIG. 4, manipulators are proximally mounted to a base of the patient side cart. Typically, the manipulator arm includes a plurality of linkages and associated joints extending between the base and the distal instrument holder. In one aspect, an example manipulator includes a plurality of joints having redundant degrees of freedom such that the joints of the manipulator arm can be driven through a range of differing configurations for a given end effector position. This may be the case for any of the embodiments of manipulator arms disclosed herein.

Figure 5A:
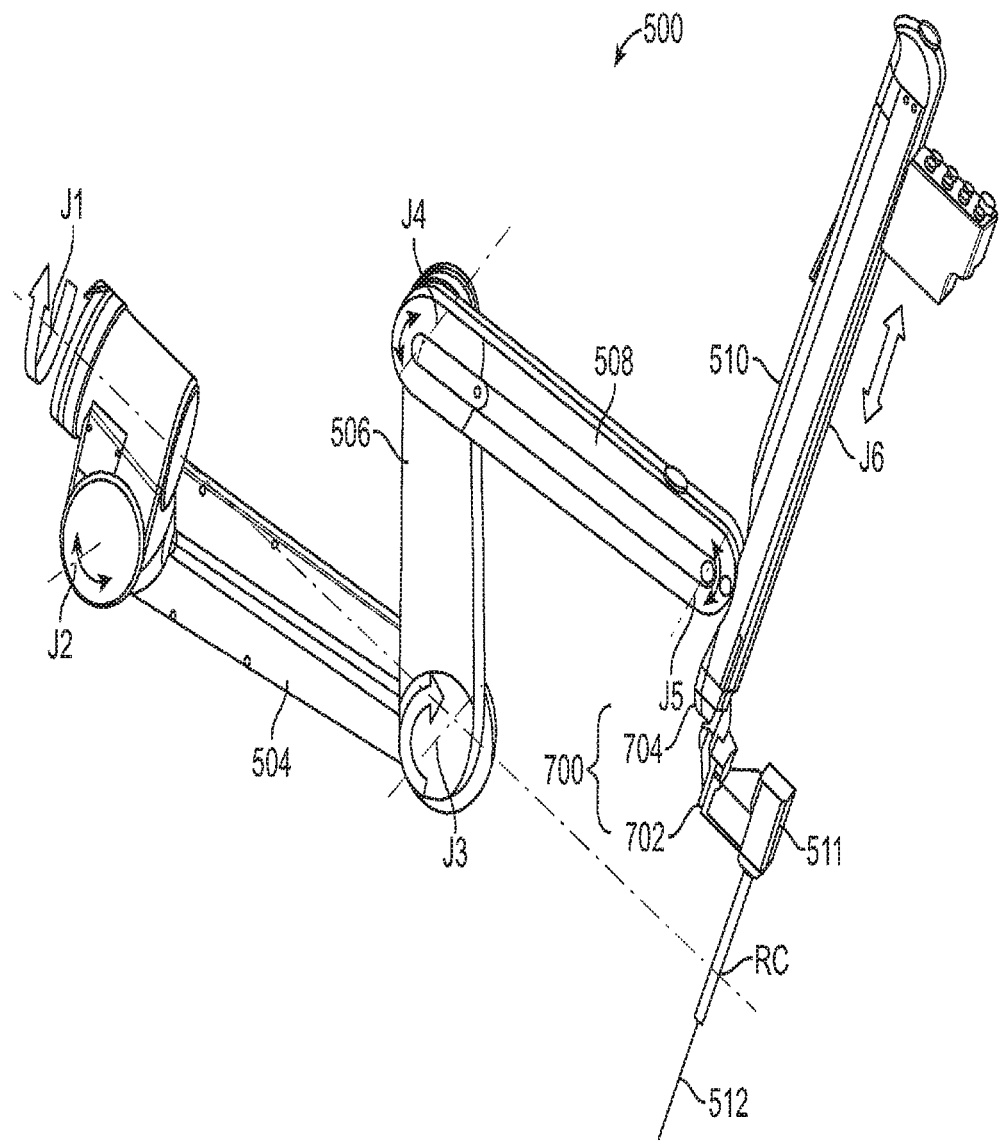

In certain embodiments, such as shown for example in FIG. 5A, an example manipulator arm includes a proximal revolute joint J1 that rotates about a first joint axis so as to revolve the manipulator arm distal of the joint about the joint axis. In some embodiments, revolute joint J1 is mounted directly to the base, while in other embodiments, joint J1 may be mounted to one or more movable linkages or joints. The joints of the manipulator, in combination, have redundant degrees of freedom such that the joints of the manipulator arm can be driven into a range of differing configurations for a given end effector position. For example, the manipulator arm of FIGS. 5A-5D may be maneuvered into differing configurations while the distal member 511 (such as a cannula through which the tool 512 or instrument shaft extends) supported within the instrument holder 510 maintains a particular state and may include a given position or velocity of the end effector. Distal member 511 is typically a cannula through which the tool shaft 512 extends, and the instrument holder 510 is typically a carriage (shown as a brick-like structure that translates on a spar) to which the instrument attaches before extending through the cannula 511 into the body of the patient through the minimally invasive aperture:

Describing the individual links of manipulator arm 500 of FIGS. 5A-5D along with the axes of rotation of the joints connecting the links as illustrated in FIG. 5A-5D, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5A. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. Typically, the pivotal axes of each of joints J2, J3, J4, and J5 are substantially parallel and the linkages appear "stacked" when positioned next to one another, as shown in FIG. 5D, so as to provide a reduced width w of the manipulator arm and improve patient clearance during maneuvering of the manipulator assembly. In some embodiments, the instrument holder also includes additional joints, such as a prismatic joint J6 that facilitates axial movement of instrument 306 through the minimally invasive aperture and facilitates attachment of the instrument holder to a cannula through which the instrument is slidably inserted.

The distal member of cannula 511 may include additional degrees of freedom distal of instrument holder 510. Actuation of the degrees of freedom of the instrument will often be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, cannula 511 includes a rotational joint J7 (not shown) near or proximal of the insertion point of the tool tip or the remote center RC about which a shaft of the tool pivots adjacent a minimally invasive aperture. A distal wrist of the instrument allows pivotal motion of an end effector of a surgical tool 512 extending through cannula 511 about instrument joints axes of one or more joints at the instrument wrist. An angle between end effector jaw elements may be controlled independently of the end effector location and orientation.

In certain embodiments, the system defines an "avoidance geometry" 700 that includes one or more reference points, segments, or volumes that correspond to the components or features of the manipulator arm. For example, the distal end of linkage 510, often called the "spar" linkage, that joins with instrument cannula 511 generally protrudes towards the patient when the tool is positioned within the surgical workspace. This feature, sometimes known as the "spar knuckle" is of concern as it could potentially contact or collide with the outer patient surface as the instrument cannula 511 rotates around its remote center RC. To avoid such collisions, therefore, the system defines the "avoidance geometry" and determines its proximity to the patient surface, typically using joint sensors from which the position or velocity of the "avoidance geometry" can be determined. Embodiments may also use proximity sensors mounted on the driven linkages or slaves that can locally sense a proximity of a patient surface. In an example embodiment, the avoidance geometry 700 includes a reference corresponding to the "spar knuckle" 702, but may include additional references corresponding to other features of the manipulator arm, such as portion 704 near the instrument wrist or a distal portion of linkage 504, that could potentially collide with a patient surface during a surgical procedure.

Figure 6A:
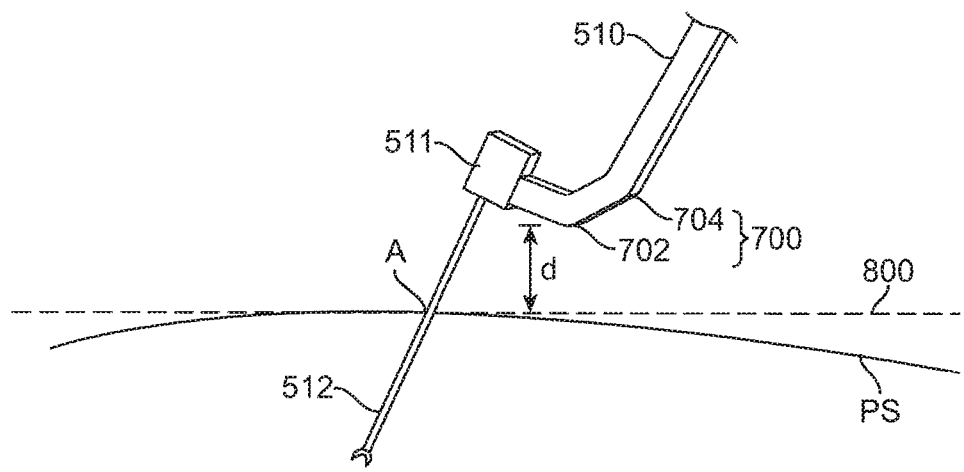
FIGS. 6A-6B show movement of the manipulator arm within a null-space and the associated distance between the avoidance geometry and obstacle surface.
Figure 6B:
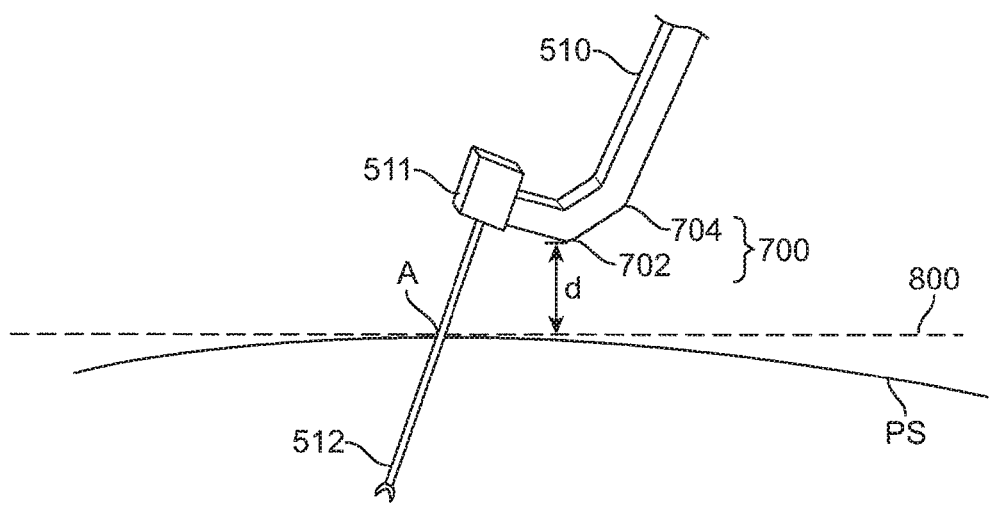

In the embodiment shown in FIGS. 6A and 6B, both an "avoidance geometry" of the manipulator arm and an "obstacle surface" corresponding to the outer patient surface is defined. In this embodiment, the location of the outer patient surface is roughly approximated by defining the obstacle surface 800 as a plane extending through the remote center, generally a horizontal plane. Since the instrument shaft of the tool pivots about the remote center which is adjacent the minimally invasive aperture it is assumed that the outer patient surface extends horizontally from the minimally invasive aperture; thus, the obstacle surface 800 most accurately represents the location of the outer patient surface at the remote center locations. The locations of the features of the manipulator arm are approximated by two reference points 702, 704, referred to collectively as avoidance geometry 700. The location and/or velocities of the avoidance geometry during commanded movement of the manipulator arm is generally determined using joint state sensors, from which the system can determine the shortest distance d between the avoidance geometry and the obstacle surface. In response to a determination that the distance d is less than desired, which may be indicative of a likely or potential arm-to-patient collision, the system calculates a coordinated avoidance movement of the joints within a null-space of a Jacobian associated with the manipulator arm so as to increase the distance d between the avoidance geometry 700 and the obstacle surface 800 and then drives the joints according to the calculated movement. Since the avoidance movement of the joints is calculated to extend within the null-space, this movement maintains the desired state of the distal portion or end effector of the manipulator arm such that the avoidance movement can be combined with the commanded movement of the manipulator arm to effect the desired state of the end effector.

Figure 7:
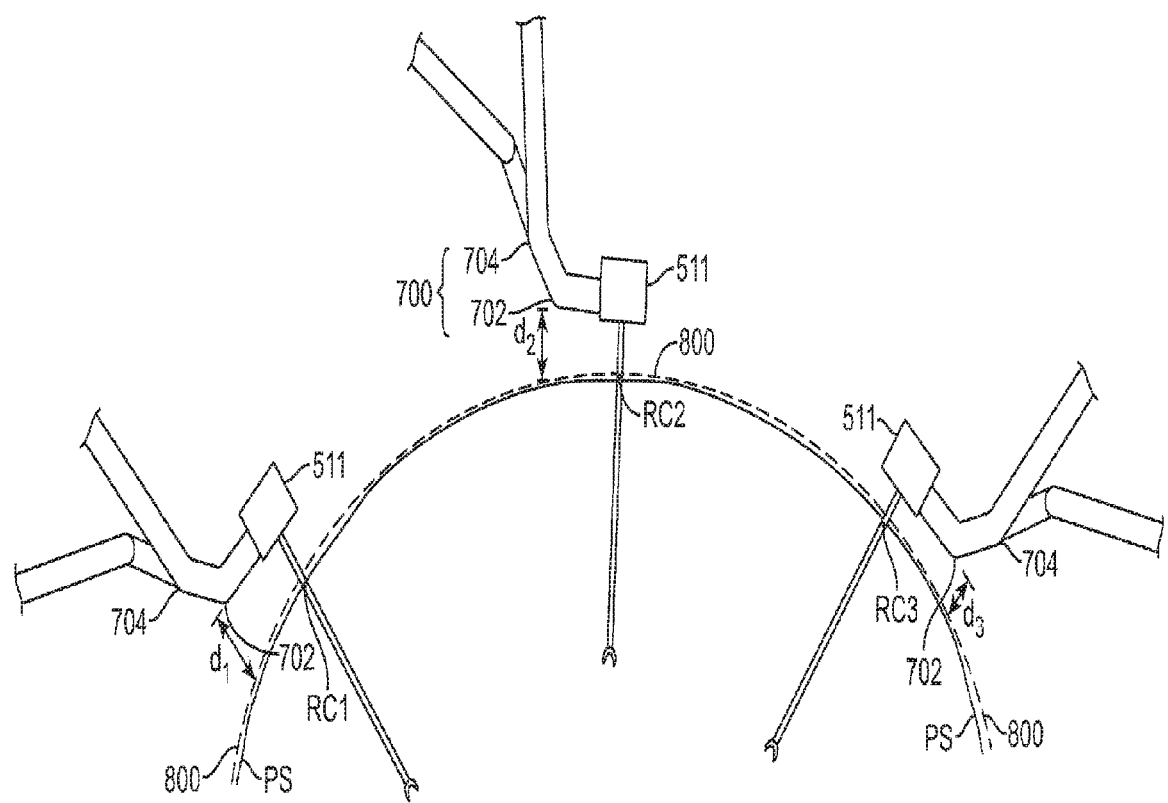
FIG. 7 shows an example system having multiple manipulator arms and an obstacle surface modeled an as to extend through the remote center of the each of the manipulator arms.
Figure 8:
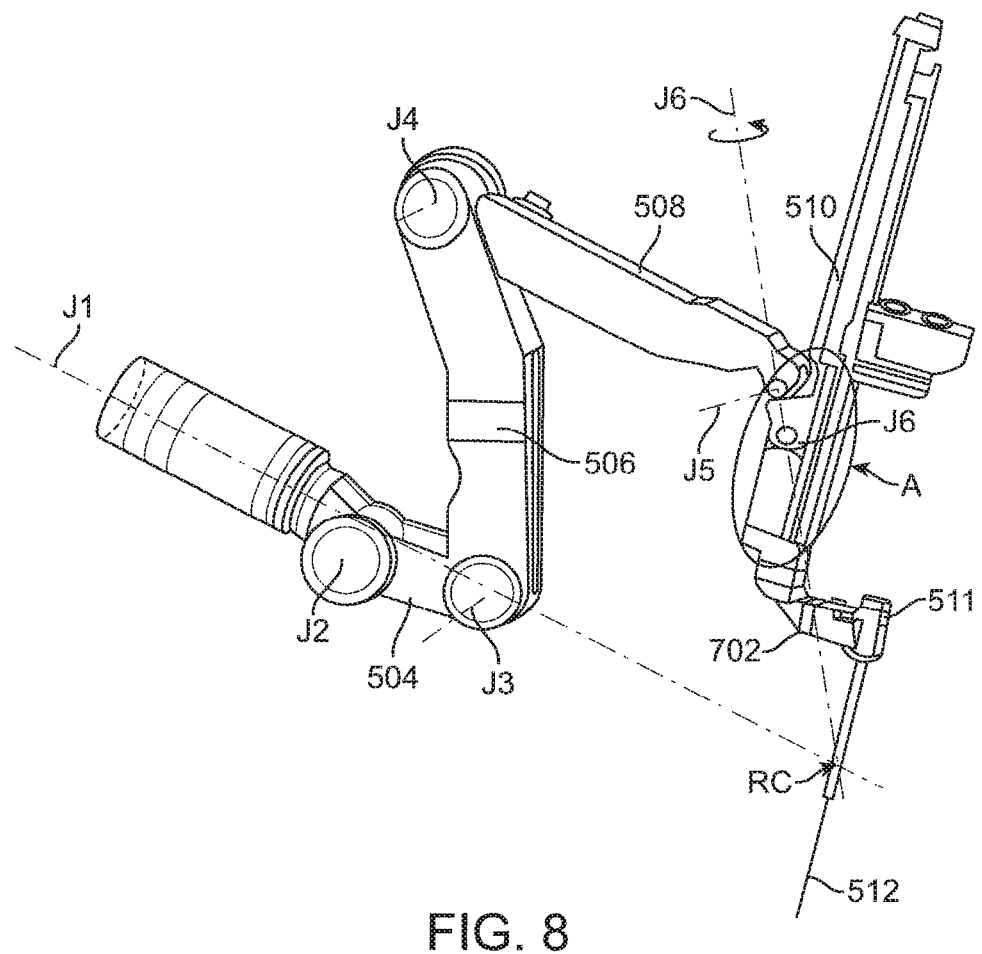
FIG. 8 shows an example manipulator arm having a revolute joint near the distal instrument holder.

In the example embodiment of FIG. 7, the obstacle surface 800 is defined as a modeled surface that more closely approximates the outer surface of a typical patient. The obstacle surface 800 may be modeled in a variety of contours or shapes corresponding to the outer patient surface or may be modeled to incorporate positional data from a variety of sources, including a joint sensor, optical sensor, or ultrasound sensor. In some embodiments, the obstacle surface 800 is approximated by extending a modeled surface through two or more remote center locations, such as shown in the obstacle surface 800 of FIG. 7, which extends through three remote centers, RC1, RC2 and RC3, and approximates a cylindrical, spherical or convex shape more closely resembling an outer surface of a typical patient at the surgical site, such as a patient torso for example. By more accurately approximating the location of the outer patient surface, the system allows for an increased range of motion for each of the three manipulator arms, while still avoiding arm-to-patient collisions by driving the joints of the manipulator arms according to a calculated avoidance movement when the shortest distance between each of the manipulators, d1, d2, and d3, is less than desired.

In accordance with many embodiments, avoidance movement may be calculated according to a number of differing methods, which can include determining "nearest points"

between the manipulator arm and the patient surface The nearest points can be determined either using calculations based on knowing the manipulator positions or states via joint sensors or can be approximated using other suitable means, such as an external sensor, video, sonar, capacitive, a touch sensor, or the like.

In one approach, the processor calculates an avoidance vector in a work space of the manipulator arms; transforms the avoidance vectors into the joint velocity space; and then projects the vectors onto the null-space using the result to obtain the avoidance movement. The processor may be configured to calculate a repulsion or avoidance vector between nearest points; map the avoidance vector into the motion of the "nearest" point of the manipulator arm and the patient surface, in the work space, and then determine the null-space coefficients ($\alpha$) that provide the desired direction and magnitude to move the nearest points away from one another. If multiple interacting points are used between various points or features on the manipulator arms and the patient surface, the resulting null-space coefficients associated with the avoidance vectors from each interacting feature can be combined through summation.

In another approach, the processor may use null-space basis vectors; transform the vectors into the motion of the avoidance geometry of the manipulator in the work space; and then combine these and the avoidance vectors in the work space into coefficients for the original null-space basis vectors. The processor may be configured to calculate a repulsion or avoidance vector between nearest points of the manipulator arm and patient surface (e.g. avoidance geometry and obstacle surface), and combine these with the avoidance vectors, as was just described. If multiple features on the manipulator arms are used, the resulting joint velocity vector or null-space coefficients can be combined using least-squares or other methodology.

Figure 9:
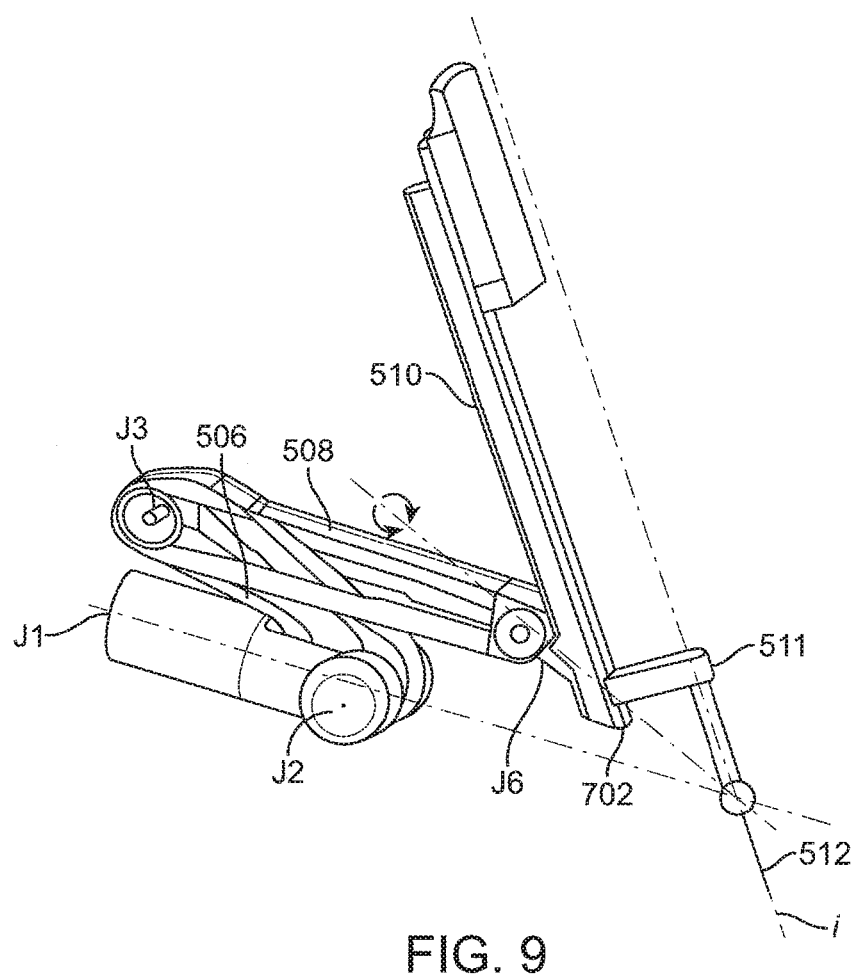
FIG. 9 shows an example manipulator arm having a revolute joint near the distal instrument holder that revolves the instrument holder.
Figure 10A:
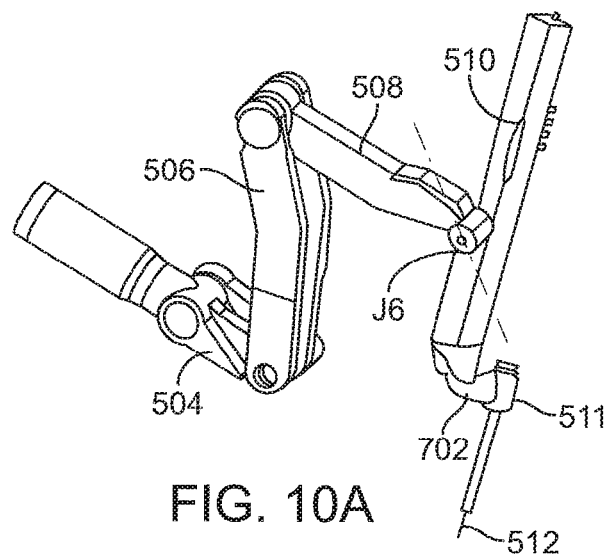
FIGS. 10A-10C show sequential views of an example manipulator arm having a revolute joint near a distal instrument holder as the joint moves throughout its range of joint movement.
Figure 10B:
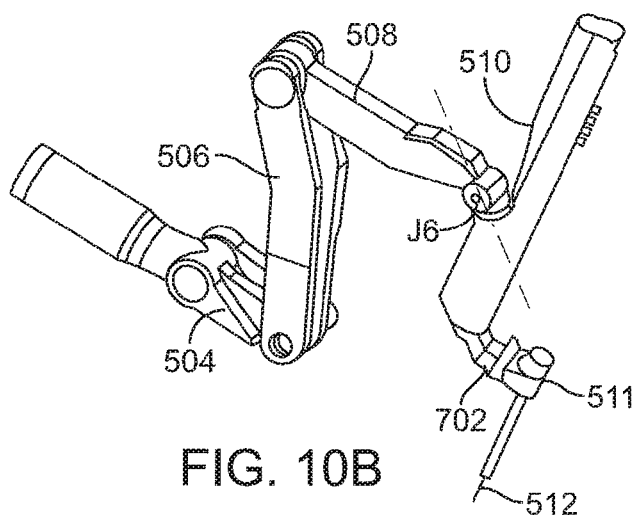
Figure 10C:
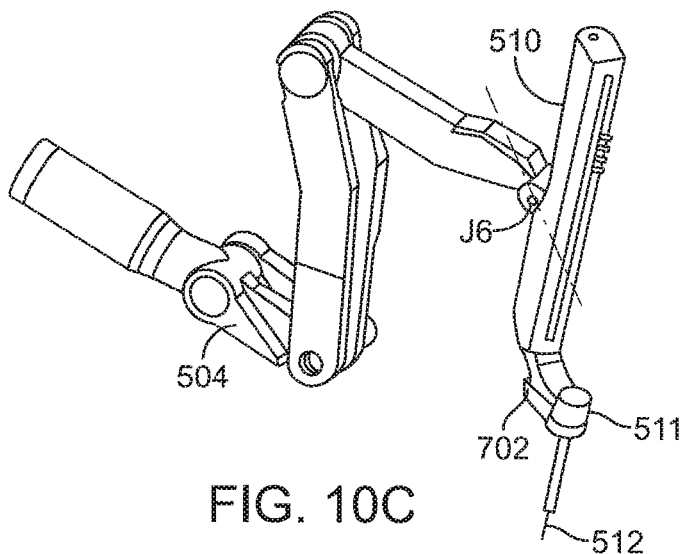

In one aspect, the avoidance movement may be calculated so as to include driving of any number of joints, or alternatively, to avoid driving particular joints of the manipulator arm. For example, in the manipulator arm shown in FIG. 8, the avoidance movement could be calculated to include driving various combinations of joints J1, J2, J3, J4 and J5 (although in the depicted embodiment joints J3, J4 and J5 are included in a parallelogram arrangement and share the same state), or alternatively could be calculated to drive joint J6, as well as any other joints needed so as to move the manipulator arm within the null-space. Joint J6 of the manipulator arm illustrated in FIG. 8 may optionally be used as the joint coupling the instrument holder 510 to a distal link of the manipulator arm 508. Joint J6 allows the instrument holder 510 to twist or revolve about the axis of joint J6, the axis typically passing through the remote center or insertion point. Ideally, the joint axis is located distally on the arm and is therefore particularly well suited to moving the orientation of the insertion axis. The addition of this redundant axis allows the manipulator to assume multiple positions for any single instrument tip position, thereby allowing the instrument tip to follow the surgeon's commands while simultaneously avoiding collisions with the patient anatomy. The relationship between the axis of joint J6, the axis of J1 and the insertion axis of a tool tip extending through cannula 511 is shown in FIG. 9. FIGS. 10A-10C show the sequential twisting or pivotal movement of the cannula 511 about the joint axis as joint J6 shifts the insertion axis of the tool tip from side to side.

Figure 11A:
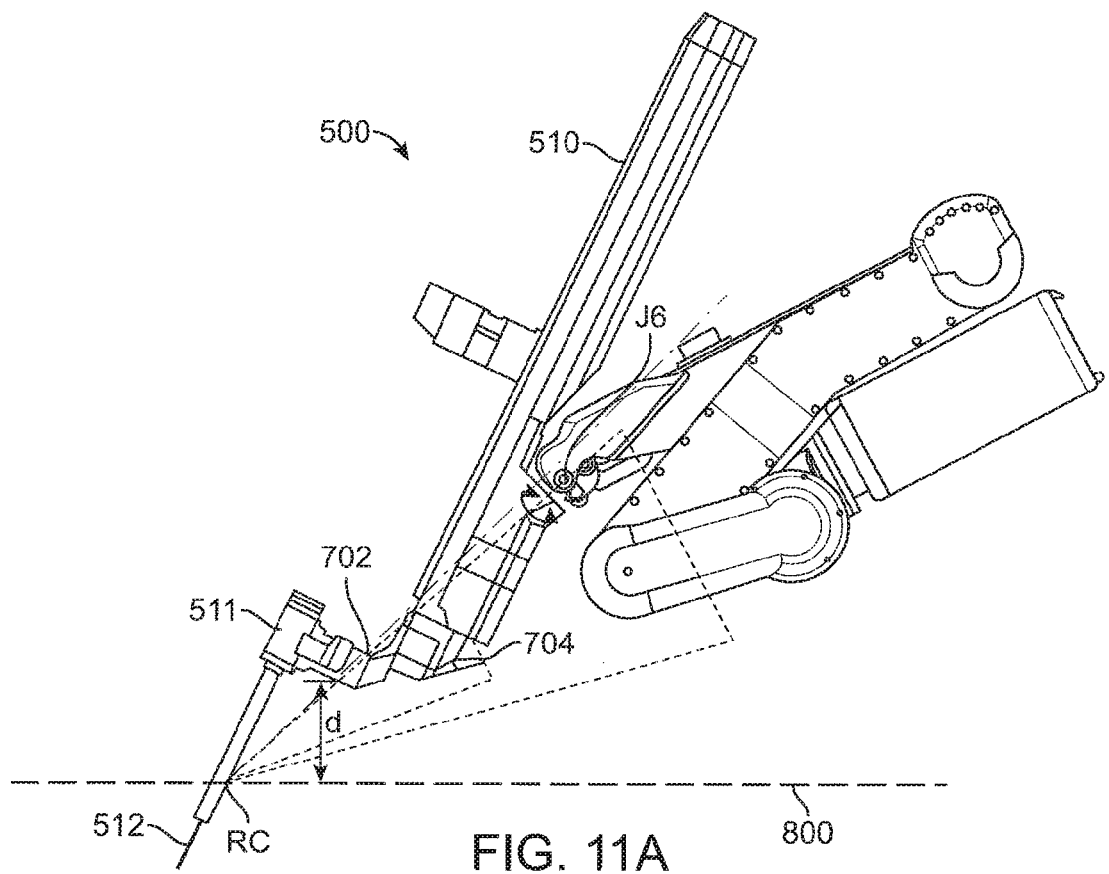
FIGS. 11A-11B show avoidance movement by driving of the distal revolute joint from an angular displacement of 0° to an angular displacement of 90°, respectively.
Figure 11B:
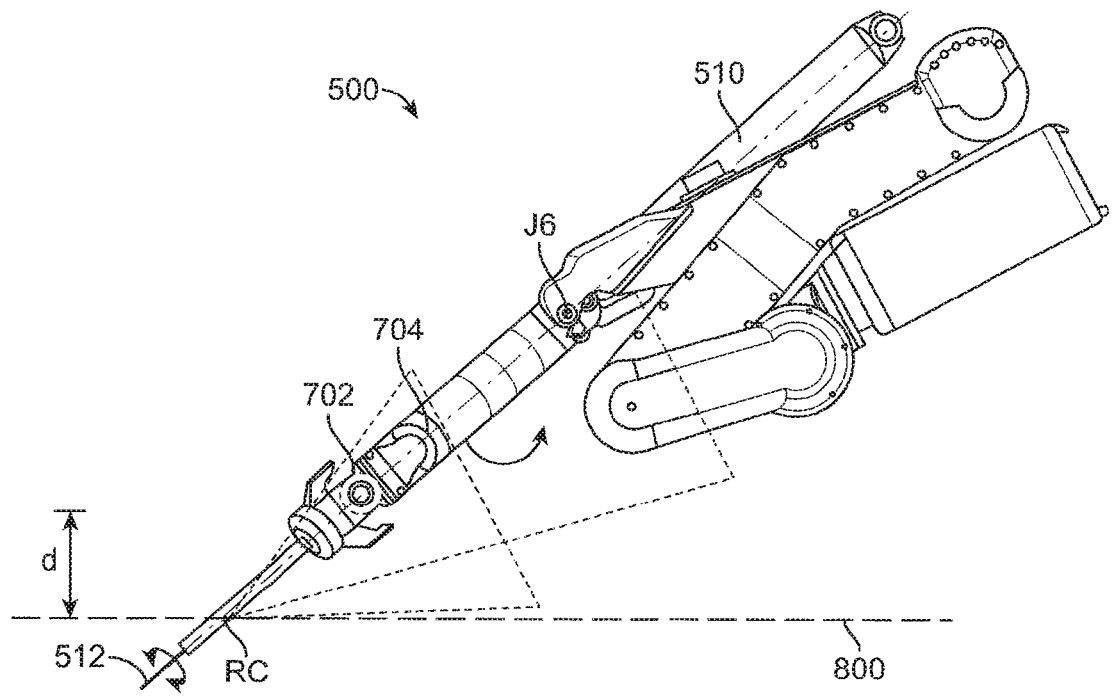

FIGS. 11A-11B illustrate one example of the use of joint J6 in accordance with the present invention. FIG. 11A illustrates the manipulator arm while the angular displacement of the joint J6 remains at 0°, at which the shortest distance between reference point 702 of avoidance geometry 700 and the obstacle surface 800 is distance d. In response to a determination that distance d is less than desired, the system calculates the avoidance movement within the null-space and drives joint J6 so as to twist or pivot cannula 511 and link 510 about the joint axis passing through the remote center RC about which cannula 511 pivots. FIG. 11B illustrates the manipulator arm with the joint J6 having been driven to an angular displacement of 90° about its axis. As shown, the motion of the cannula 511 has increased the distance d between the nearest point 702 of the avoidance geometry and the obstacle surface 800. Thus, the present invention can inhibit arm-to-patient collisions by calculating the avoidance movement to include driving of a distal joint, such as joint J6.

In an example embodiment, the joint movements of the manipulator are controlled by driving one or more joints by a controller using motors of the system, the joints being driven according to coordinated and joint movements calculated by a processor of the controller. Mathematically, the controller may perform at least some of the calculations of the joint commands using vectors and/or matrices, some of which may have elements corresponding to configurations or velocities of the joints. The range of alternative joint configurations available to the processor may be conceptualized as a joint space. The joint space may, for example, have as many dimensions as the manipulator has degrees of freedom and a particular configuration of the manipulator may represent a particular point in the joint space with each coordinate corresponding to a joint state of an associated joint of the manipulator.

In an example embodiment, the system includes a controller in which a Cartesian-space commanded position and velocity are inputs. Although generally, there is no closed form relationship which maps a desired Cartesian-space position to an equivalent joint-space position, there is generally a closed form relationship between the Cartesian-space and joint-space velocities, such that a kinematic Jacobian can be used to map joint-space velocities to Cartesian-space velocities. Thus, even when there is no closed-form mapping between input and output positions, mappings of the velocities of the joint can iteratively be used, such as in a Jacobian-based controller, to implement a movement of the manipulator from a commanded user input, however a variety of implementations can be used.

In an example embodiment, the system includes a controller in which a commanded position and velocity of a feature in the work-space, denoted here as its Cartesian space, are inputs. The feature may be any feature on the manipulator or off the manipulator which can be used as a control frame to he articulated using control inputs. An example of a feature on the manipulator, used in various examples described herein, would be the tool-tip. Another example of a feature on the manipulator would be a physical feature which is not on the tool-tip, but is a part of the manipulator, such as a pin or a painted pattern. An example of a feature off the manipulator would be a reference point in empty space which is exactly a certain distance and angle away from the tool-tip. Another example of a feature off the manipulator would be a target tissue whose position relative to the manipulator can be established. In all these cases, the end effector is associated with an imaginary control frame which is to be articulated using control inputs. However, in the following, the "end effector" and the "tool tip" are used synonymously. Although generally, there is no closed form relationship which maps a desired Cartesian space end effector position to an equivalent joint-space position, there is generally a closed form relationship between the Cartesian space end effector and joint-space velocities. The kinematic Jacobian is the matrix of partial derivatives of Cartesian space position elements of the end effector with respect to joint space position elements. In this way, the kinematic Jacobian captures the kinematic relationship between the end effector and the joints. In other words, the kinematic Jacobian captures the effect of joint motion on the end effector. The kinematic Jacobian (J) can be used to map joint-space velocities (dq/dt) to Cartesian space end effector velocities (dx/dt) using the relationship below:

$$dx/dt = J\, dq/dt$$

Thus, even when there is no closed-form mapping between input and output positions, mappings of the velocities can iteratively be used, such as in a Jacobian-based controller to implement a movement of the manipulator from a commanded user input, however a variety of implementations can be used. Although many embodiments include a Jacobian-based controller, some implementations may use a variety of controllers that may be configured to access the Jacobian to provide any of the features described herein.

One such implementation is described in simplified terms below. The commanded joint position is used to calculate the Jacobian (J). During each time step ($\Delta t$) a Cartesian space velocity (dx/dt) is calculated to perform the desired move ($dx_{des}/dt$) and to correct for built up deviation ($\Delta x$) from the desired Cartesian space position. This Cartesian space velocity is then converted into a joint-space velocity (dq/dt) using the pseudo-inverse of the Jacobian ($J^\#$). The resulting joint-space commanded velocity is then integrated to produce joint-space commanded position (q). These relationships are listed below:

$$dx/dt = dx_{des}/dt + k\Delta x \quad (1)$$

$$dq/dt = J^\# dx/dt \quad (2)$$

$$q_i = q_{i-1} + dq/dt\, \Delta t \quad (3)$$

The pseudo-inverse of the Jacobian (J) directly maps the desired tool tip motion (and, in some cases, a remote center of pivotal tool motion) into the joint velocity space. If the manipulator being used has more useful joint axes than tool tip degrees of freedom (up to six), (and when a remote center of tool motion is in use, the manipulator should have an additional 3 joint axes for the 3 degrees of freedom associated with location of the remote center), then the manipulator is said to be redundant. A redundant manipulator's Jacobian includes a "null-space" having a dimension of at least one. In this context, the "null-space" of the Jacobian (N(J)) is the space of joint velocities which instantaneously achieves no tool tip motion (and when a remote center is used, no movement of the pivotal point location); and "null-motion" is the combination, trajectory, or path of joint positions which also produces no instantaneous movement of the tool tip and/or location of the remote center. Incorporating or injecting the calculated null-space velocities into the control system of the manipulator to achieve the desired reconfiguration of the manipulator including any reconfigurations described herein) changes above equation (2) to:

$$dq/dt = dq_{perp}/dt\, dq_{null}/dt \quad (4)$$

$$dq_{perp}/dt = dx/dt \quad (5)$$

$$dq_{null}/dt = (1 - J^\# J)z = V_n V_n^T z = V_n \alpha \quad (6)$$

Figure 12A:
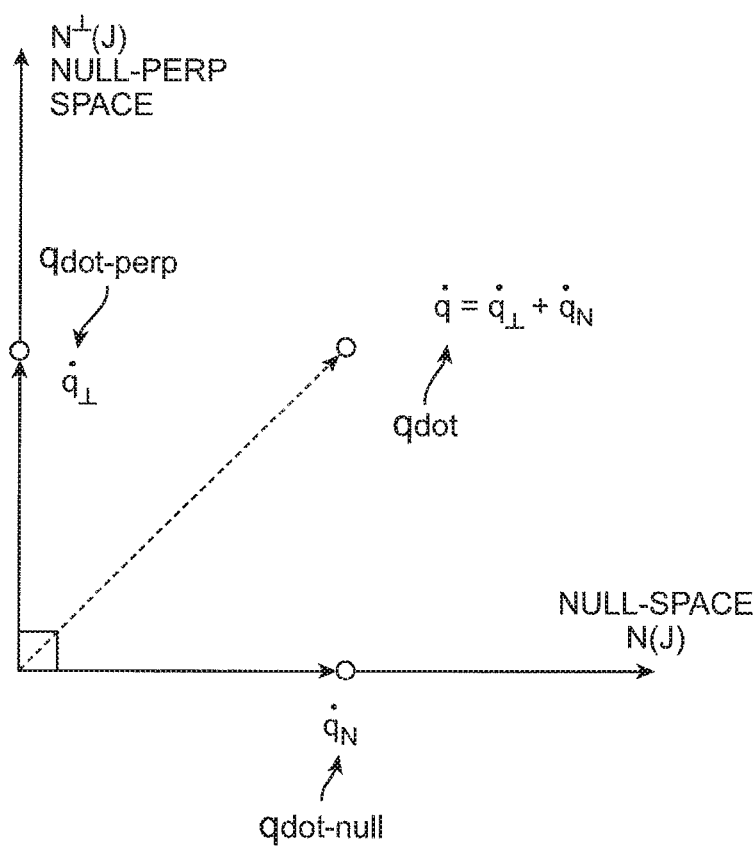
FIGS. 12A-12B graphically represent the relationship between the null-space and the null-perpendicular-space of the Jacobian for an example manipulator assembly.

The joint velocity according to Equation (4) has two components: the first being the null-perpendicular-space component, the "purest" joint velocity (shortest vector length) which produces the desired tool tip motion (and when the remote center is used, the desired remote center motion); and the second being the null-space component. Equations (2) and (5) show that without a null-space component, the same equation is achieved. Equation (6) starts with a traditional form for the null-space component on the left, and on the far right side, shows the form used in an example system, wherein ($V_n$) is the set of orthonormal basis vectors for the null-space, and ($\alpha$) are the coefficients for blending those basis vectors. In some embodiments, a is determined by control parameters, variables or setting, such as by use of knobs or other control means, to shape or control the motion within the null-space as desired, FIG. 12A graphically illustrates the relationship between the null-space of the Jacobian and the null-perpendicular-space of the Jacobian. FIG. 12A shows a two-dimensional schematic showing the null-space along the horizontal axis and the null-perpendicular-space along the vertical axis, the two axes being orthogonal to one another. The diagonal vector represents the sum of a velocity vector in the null-space and a velocity vector the null-perpendicular-space, which is representative of Equation (4) above.

Figure 12B:
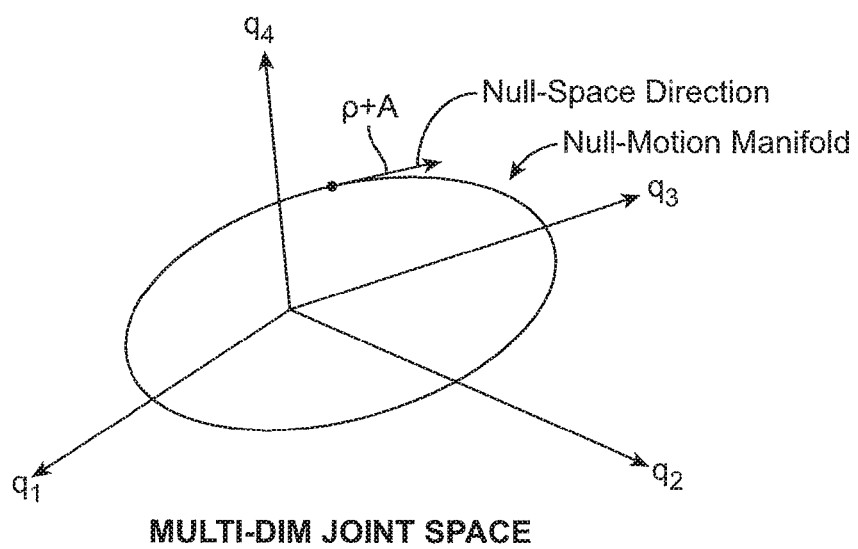

FIG. 12B graphically illustrates the relationship between the null-space and the null-motion manifold within a four-dimensional joint space, shown as the "null-motion manifold." Each arrow (q1, q2, q3, and q4) represents a principal joint axis. The closed curve represents a null-motion manifold which is a set of joint-space positions that instantaneously achieves the end effector position. For a given point A on the curve, since the null-space is a space of joint velocities that instantaneously produces no movement of the end effector, the null-space is parallel to the tangent of the null-motion manifold at point A. In an example embodiment, calculating the avoidance movement includes generating null-space coefficients ($\alpha$) which increases the distance between the avoidance geometry and the obstacle surface, thereby increasing the manipulator arm to patient distance.

In one approach, this is accomplished by generating a potential field in joint-space, such that high potentials represent shorter distances between the manipulator arm and the outer patient surface, and lower potentials represent larger distances. The null-space coefficients ($\alpha$) are then chosen to descend down the negative gradient of the potential field, preferably to the greatest extent possible. In a second approach, the system determines the null-space basis vectors and maps the null-space basis vectors into the resulting motion of the avoidance geometry in the work space and then selects the null-space coefficients for each basis vector increases the distance between the avoidance geometry and the obstacle surface, thereby increasing the overall manipulator arm to patient distance.

Figure 13:
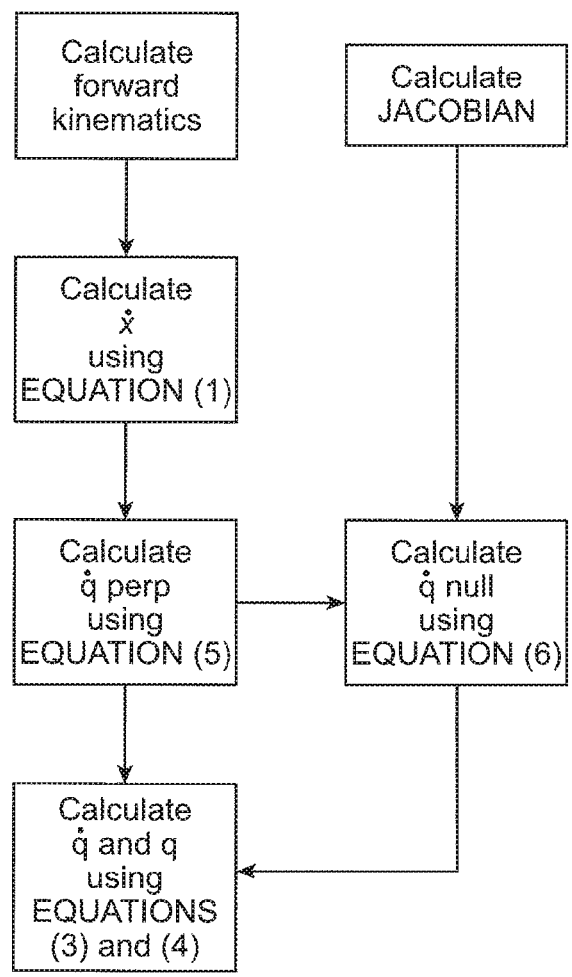
FIGS. 13-14 are simplified block diagrams representing methods in accordance with many embodiments.
Figure 14:
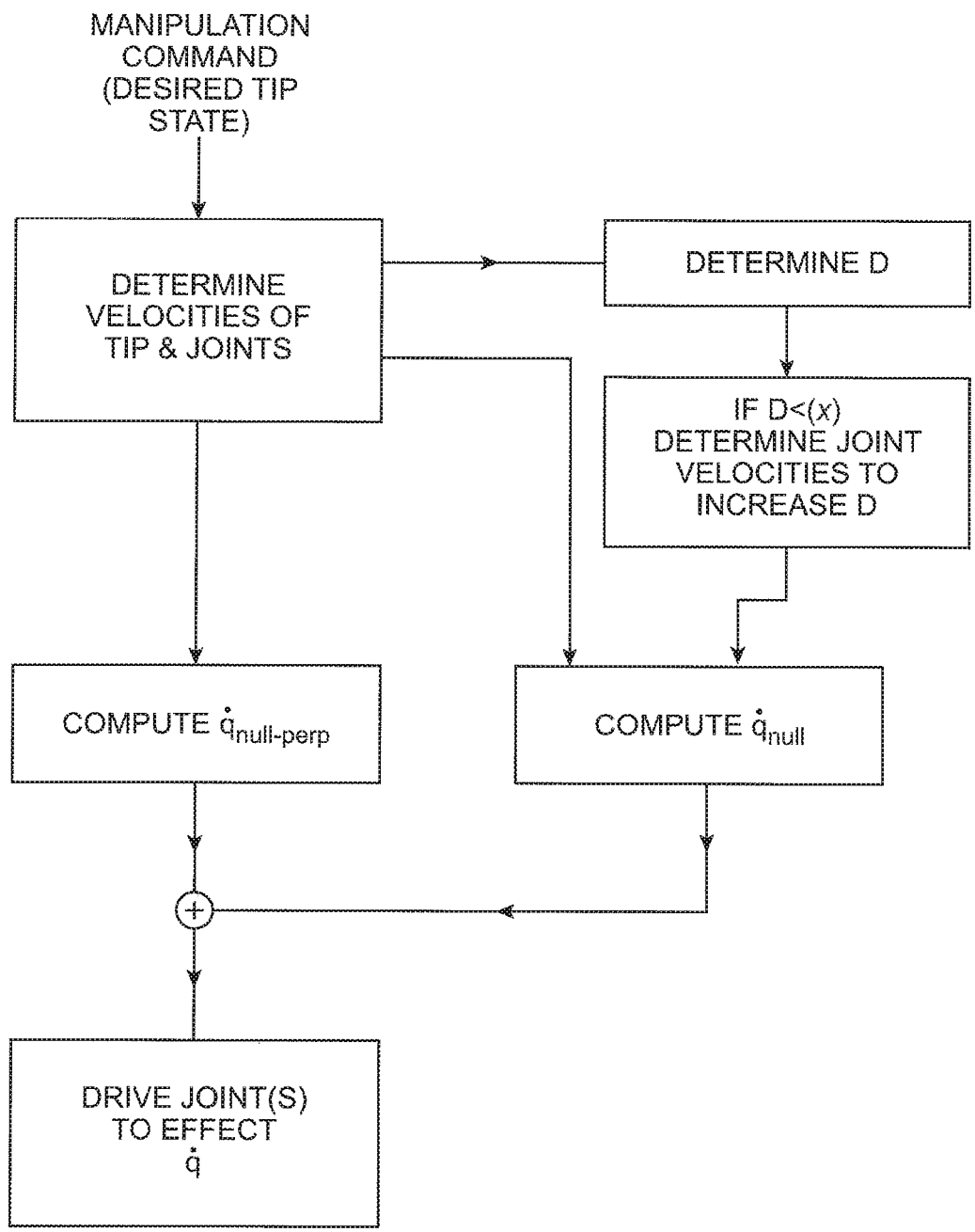

FIGS. 13-14 illustrate methods of reconfiguring a manipulator assembly of a robotic surgical system to avoid arm-to-patient collisions in accordance with many embodiments of the present invention. FIG. 13 shows a simplified schematic of the required blocks need to implement the general algorithms to control the patient side cart joint states, in relation to the equations discussed above. According to the method of FIG. 13, the system: calculates the forward kinematics of the manipulator arm; then calculates dx/dt using Equation (1), calculates $dq_{perp}/dt$ using Equation (5); and then calculates $dq_{null}/dt$ based on the description in the preceding paragraph and using Equation (6). From the calculated $dq_{perp}/dt$ and $dq_{null}/dt$, the system calculates dq/dt and q using Equations (4) and (3), respectively, thereby providing the movement by which the controller can affect the desired reconfiguration of the manipulator while maintaining the desired state of the end effector and/or location of the remote center.

FIG. 14 shows a block diagram of an example embodiment of the system. In response to a manipulation command input by a user to effect a desired tip state, the system uses the present joint position, which may be determined using joint state sensors, to compute the appropriate Jacobian and hence $dq_{perp}/dt$ to effect the desired tip state. The present joint positions can also be used to determine a distance D between an avoidance geometry of the manipulator arm and an obstacle surface corresponding to an outer patient surface. In response to a determination that a distance D between the avoidance geometry of the manipulator arm and an obstacle surface corresponding to an outer patient surface is less than a critical distance ($D_{min}$), the system determines joints velocities $dq_{null}/dt$ that increase D, which can then be combined with $dq_{perp}/dt$ to obtain dq/dt, according to which the joint(s) are driven to effect the desired tip state concurrent with avoiding arm-to-patient collisions.

While the example embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A system comprising:
a base;
a manipulator arm comprising a proximal portion coupled to the base, a movable distal portion, and a plurality of joints between the base and the distal portion, the plurality of joints together having sufficient degrees of freedom to allow a range of different joint states of the plurality of joints for a given pose of the distal portion of the manipulator arm;
an input device; and
a processor-based controller coupled to the manipulator arm and to the input device, the controller being configured to perform operations including:
receiving a manipulation command from the input device to move the distal portion of the manipulator arm with a first movement at a surgical work site of a patient;
calculating a displacing movement of the plurality of joints of the manipulator arm in response to the manipulation command so as to implement the first movement, wherein calculating the displacing movement comprises calculating joint movement within a null-perpendicular space of a Jacobian, the null-perpendicular space being orthogonal to a null-space of the Jacobian;
calculating an avoidance movement of the plurality of joints of the manipulator arm within the null-space of the Jacobian so as to implement a clearance between the manipulator arm and an outer surface of the patient within a range of motion of the manipulator arm; and
driving the plurality of joints of the manipulator arm according to the displacing movement and the avoidance movement.

2. The system of claim 1, wherein the controller is further configured to calculate a distance between an avoidance geometry of the manipulator arm and an obstacle surface, the obstacle surface corresponding to the patient outer surface, and the avoidance geometry corresponding to a portion of the manipulator for which clearance from the patient outer surface is desired.

3. The system of claim 2, wherein the controller is further configured to drive the plurality of joints according to the calculated avoidance movement in response to a determination by the controller that the distance between the avoidance geometry and obstacle surface is less than desired.

4. The system of claim 2, wherein
the distal portion comprises a surgical instrument having an elongate shaft extending distally to a surgical end effector;
the displacing movement is calculated to effect a desired end effector state; and
the avoidance movement of the plurality of joints is calculated so as to maintain the desired end effector state.

5. The system of claim 2, wherein
the manipulator arm is configured to support a tool having a shaft with an intermediate portion extending along an insertion axis of the tool to a distal end effector; and
at least some joints of the plurality of joints mechanically constrain movement of the distal portion relative to the base so that the distal portion of the manipulator arm pivots about a remote center disposed adjacent the insertion axis to facilitate movement of the end effector within the surgical work site, wherein the work site is accessed through an insertion opening.

6. The system of claim 5, wherein the controller is further configured to determine the obstacle surface by approximating or modeling a surface that intersects with the remote center.

7. The system of claim 5, wherein
the system comprises one or more additional manipulator arms, each having a remote center; and
the processor is configured to determine the obstacle surface by approximating or modeling the surface so as to intersect with each of the remote center positions.

8. The system of claim 1, wherein the controller is configured to calculate end effector displacing movement so as to not drive one or more joints and to calculate the avoidance movement so as to include driving of the one or more joints.

9. The system of claim 8, wherein the one or more joints includes a first joint that pivots the insertion axis about an axis of the first joint, the axis extending through the remote center.

10. The system of claim 9, wherein an intermediate link is disposed proximal of and adjacent to the distal portion with the first joint therebetween, the first joint comprising a revolute joint mechanically constraining movement of the distal portion relative to the intermediate link to rotation about a first joint axis, the first joint axis extending from a second joint distally toward the intermediate link so as to intersect the insertion axis through the remote center.

11. A system comprising:
a base;
a manipulator arm comprising a proximal portion coupled to the base, a movable distal portion, and a plurality of joints that kinematically couple a plurality of links between the base and the distal portion, the plurality of links together having sufficient degrees of freedom to allow a range of different link states of the plurality of links for a given pose of the distal portion of the manipulator arm;
an input device; and a processor-based controller coupled to the manipulator arm and to the input device, the controller being configured to perform operations including:

receiving a manipulation command from the input device to move the distal portion of the manipulator arm with a first movement at a surgical work site of a patient;

calculating a displacing movement of the plurality of joints of the manipulator arm in response to the manipulation command so as to implement the first movement, wherein calculating the displacing movement comprises calculating link movement within a null-perpendicular space of a Jacobian, the null-perpendicular space being orthogonal to a null-space of the Jacobian;

calculating an avoidance movement of the plurality of links of the manipulator arm within the null-space of the Jacobian so as to implement a clearance between the manipulator arm and an outer surface of the patient within a range of motion of the manipulator arm; and driving the plurality of joints that kinematically couple the plurality of links of the manipulator arm according to the displacing movement and the avoidance movement.

12. The system of claim 11, wherein the controller is further configured to calculate a distance between an avoidance geometry of the manipulator arm and an obstacle surface, the obstacle surface corresponding to the patient outer surface, and the avoidance geometry corresponding to a portion of the manipulator for which clearance from the patient outer surface is desired.

13. The system of claim 12, wherein the controller is further configured to drive the plurality of joints according to the calculated avoidance movement in response to a determination by the controller that the distance between the avoidance geometry and obstacle surface is less than desired.

14. The system of claim 12, wherein
the distal portion comprises a surgical instrument having an elongate shaft extending distally to a surgical end effector;
the displacing movement is calculated to effect a desired end effector state; and
the avoidance movement of the plurality of joints is calculated so as to maintain the desired end effector state.

15. The system of claim 12, wherein
the manipulator arm is configured to support a tool having a shaft with an intermediate portion extending along an insertion axis of the tool to a distal end effector; and
at least some joints of the plurality of joints mechanically constrain movement of the distal portion relative to the base so that the distal portion of the manipulator arm pivots about a remote center disposed adjacent the insertion axis to facilitate movement of the end effector within the surgical work site, wherein the work site is accessed through an insertion opening.

16. The system of claim 15, wherein the controller is further configured to determine the obstacle surface by approximating or modeling a surface that intersects with the remote center.

17. The system of claim 15, wherein
the system comprises one or more additional manipulator arms, each having a remote center; and
the processor is configured to determine the obstacle surface by approximating or modeling the surface so as to intersect with each of the remote center positions.

18. The system of claim 11, wherein the controller is configured to calculate end effector displacing movement so as to not drive one or more joints and to calculate the avoidance movement so as to include driving of the one or more joints.

19. The system of claim 18, wherein the one or more joints includes a first joint that pivots the insertion axis about an axis of the first joint, the axis extending through the remote center.

20. The system of claim 19, wherein an intermediate link is disposed proximal of and adjacent to the distal portion with the first joint therebetween, the first joint comprising a revolute joint mechanically constraining movement of the distal portion relative to the intermediate link to rotation about a first joint axis, the first joint axis extending from a second joint distally toward the intermediate link so as to intersect the insertion axis through the remote center.

* * * * *